(12) United States Patent
Hasebe et al.

(10) Patent No.: US 9,809,668 B2
(45) Date of Patent: Nov. 7, 2017

(54) POLYMERIZABLE COMPOUND, COMPOSITION, POLYMER, OPTICALLY ANISOTROPIC BODY, LIQUID CRYSTAL DISPLAY DEVICE, AND ORGANIC EL DEVICE

(71) Applicant: DIC CORPORATION, Tokyo (JP)

(72) Inventors: Hiroshi Hasebe, Kita-adachi-gun (JP); Yoshio Aoki, Kita-adachi-gun (JP); Kunihiko Kotani, Kita-adachi-gun (JP); Akihiro Koiso, Kita-adachi-gun (JP); Hidetoshi Nakata, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 15/039,972

(22) PCT Filed: Nov. 27, 2014

(86) PCT No.: PCT/JP2014/081442
§ 371 (c)(1),
(2) Date: May 27, 2016

(87) PCT Pub. No.: WO2015/080219
PCT Pub. Date: Jun. 4, 2015

(65) Prior Publication Data
US 2017/0002123 A1    Jan. 5, 2017

(30) Foreign Application Priority Data

Nov. 29, 2013 (JP) ................. 2013-248407

(51) Int. Cl.
*C08F 2/46* (2006.01)
*C08F 2/50* (2006.01)
*C08G 61/04* (2006.01)
*C08F 220/38* (2006.01)
*C09K 19/38* (2006.01)
*G02F 1/13363* (2006.01)
*G02B 5/30* (2006.01)
*C09K 19/34* (2006.01)
*C07D 277/66* (2006.01)
*C09K 19/56* (2006.01)
*H01L 51/00* (2006.01)
*H01L 51/52* (2006.01)
*C09K 19/04* (2006.01)
*C08F 220/10* (2006.01)
*C08F 222/10* (2006.01)

(52) U.S. Cl.
CPC .......... *C08F 220/38* (2013.01); *C07D 277/66* (2013.01); *C09K 19/34* (2013.01); *C09K 19/348* (2013.01); *C09K 19/3477* (2013.01); *C09K 19/3497* (2013.01); *C09K 19/38* (2013.01); *C09K 19/56* (2013.01); *G02B 5/30* (2013.01); *G02B 5/3083* (2013.01); *G02F 1/13363* (2013.01); *H01L 51/004* (2013.01); *H01L 51/5281* (2013.01); *C08F 220/10* (2013.01); *C08F 2220/387* (2013.01); *C08F 2222/1013* (2013.01); *C09K 2019/0448* (2013.01)

(58) Field of Classification Search
CPC .............. C08F 220/38; C08F 2220/387; C08F 2222/1013; C08F 220/10; C09K 19/57; C09K 19/38; C09K 19/34; C09K 19/384; C09K 2019/0448; C09K 19/3477; C09K 19/3497
USPC ........... 522/39, 33, 6, 71, 189, 184, 1; 520/1
See application file for complete search history.

(56) References Cited

FOREIGN PATENT DOCUMENTS

| JP | 2009-173893 A | | 8/2009 |
|---|---|---|---|
| JP | 2009-227667 | * | 10/2009 |
| JP | 2009-227667 A | | 10/2009 |
| JP | 2010-30979 A | | 2/2010 |
| JP | 2010-241919 A | | 10/2010 |
| JP | 2011-6361 A | | 1/2011 |
| JP | 2011-42606 A | | 3/2011 |
| JP | 2011-150314 A | | 8/2011 |
| JP | 2011-162678 | * | 8/2011 |
| JP | 2011-162678 A | | 8/2011 |
| JP | 2011-207765 A | | 10/2011 |
| JP | 2013-509458 A | | 3/2013 |

OTHER PUBLICATIONS

Kobayashi et al, JP 2009-227667 Machine Translation Part 1, Oct. 8, 2009.*
Kobayashi et al, JP 2009-227667 Machine Translation Part 2, Oct. 8, 2009.*
Okawa et al, JP 2011-162678 Machine Translation Part 1, Aug. 25, 2011.*
Okawa et al, JP 2011-162678 Machine Translation Part 2, Aug. 25, 2011.*
International Serach Report dated Feb. 24, 2015, issued in counterpart of International application No. PCT/JP2014/08144(2 pages).

* cited by examiner

*Primary Examiner* — Jessica E Whiteley
(74) *Attorney, Agent, or Firm* — Westerman, Hattori, Daniels & Adrian, LLP

(57) ABSTRACT

It is an object of the present invention to provide a polymerizable compound suitable as a material for optically anisotropic bodies having excellent optical properties, a composition containing the polymerizable compound, a polymer obtained by polymerizing the polymerizable compound, an optically anisotropic body formed of the polymer, and a liquid crystal display device including the optically anisotropic body.

9 Claims, No Drawings

POLYMERIZABLE COMPOUND, COMPOSITION, POLYMER, OPTICALLY ANISOTROPIC BODY, LIQUID CRYSTAL DISPLAY DEVICE, AND ORGANIC EL DEVICE

TECHNICAL FIELD

The present invention relates to a polymerizable compound, a composition, a polymer, an optically anisotropic body, a liquid crystal display device, and an organic EL device.

BACKGROUND ART

Optically anisotropic bodies such as retardation films and polarizing plates used in liquid crystal displays can be produced by applying a solution containing a polymerizable liquid crystal material onto a substrate subjected to a rubbing treatment or a substrate having a photo-alignment film formed thereon, drying a solvent, and then performing polymerization using ultraviolet rays or heat. Regarding retardation films, the wavelength dispersion of the birefringence index ($\Delta n$) needs to be decreased or reversed in order to improve the viewing angle of liquid crystal displays. To realize such characteristics, a reverse dispersion-type polymerizable liquid crystal compound has been developed (e.g., PTL 1). Herein, the wavelength $\lambda$ of incident light on a retardation film is illustrated on the horizontal axis and the birefringence index ($\Delta n$=refractive index $n_e$ for extraordinary ray–refractive index no for ordinary ray) of the retardation film is illustrated on the vertical axis. When the slope of a graph obtained by plotting the birefringence index against the wavelength is positive (diagonally upward to the right), it is generally said that the wavelength dispersion of the birefringence index is "reverse" or the polymerizable liquid crystal compound constituting the retardation film is a reverse dispersion-type polymerizable liquid crystal compound.

CITATION LIST

Patent Literature

PTL 1: Japanese Unexamined Patent Application Publication (Translation of PCT Application) No. 2013-509458

SUMMARY OF INVENTION

Technical Problem

A method for providing the polymerizable compound constituting the retardation film as a reverse dispersion-type polymerizable compound is to intramolecularly introduce a moiety (vertical unit) having a large birefringence index in a direction vertical to the major axis of a molecule. However, the introduction of the vertical unit tends to degrade the liquid crystallinity and cause crystallization. Therefore, a polymerizable compound having desired properties can only be obtained after much trial and error.

A heating temperature at which the polymerizable compound is polymerized is an important factor that affects the performance of the retardation film. When the heating temperature is decreased, it is believed that the degradation of the film is suppressed and thus the optical properties are improved. However, the reverse dispersion-type polymerizable compound into which a bulky moiety (the vertical unit) is introduced in a direction vertical to the major axis of a molecule mainly including an inflexible mesogen exhibits a liquid crystalline phase at a very high temperature. This poses a problem in that, when desired optical properties are achieved by polymerizing a reverse dispersion-type liquid crystal and uniformly aligning the polymerizable compound in the formed film, the polymerization requires heating at a relativity high temperature.

In view of the foregoing, it is an object of the present invention to provide a polymerizable compound suitable as a material for optically anisotropic bodies having excellent optical properties, a composition containing the polymerizable compound, a polymer obtained by polymerizing the polymerizable compound, an optically anisotropic body formed of the polymer, and a liquid crystal display device including the optically anisotropic body.

Solution to Problem

According to a first aspect of the present invention, there is provided a polymerizable compound represented by general formula (1) below.

[Chem. 1]

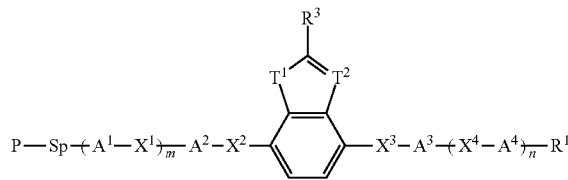

(1)

[(in the formula, P represents a polymerizable functional group and Sp represents a spacer group or a single bond, $A^1$, $A^2$, $A^3$, and $A^4$ each independently represent a divalent alicyclic hydrocarbon group or aromatic hydrocarbon group, $X^1$, $X^2$, $X^3$, and $X^4$ each independently represent a divalent linking group or a single bond (at least one of $X^1$, $X^2$, $X^3$, and $X^4$ represents one of linking groups selected from —$CH_2CH_2COO$—, —$CH_2CH_2OCO$—, —$COOCH_2CH_2$—, —$OCOCH_2CH_2$—, —CH=CH—, —C≡C—, —CH=CHCOO—, —OCOCH=CH—, —N=N—, —C=N—, —N=C—, and —C=N—N=C—), $R^1$ represents an alkyl group having 1 to 12 carbon atoms, an alkoxy group having 1 to 12 carbon atoms, or "*-Sp-P" (* represents a bond with $A^4$ or $A^3$), $R^3$ represents an alkyl group having 1 to 6 carbon atoms, an alicyclic hydrocarbon group, or an aromatic hydrocarbon group, wherein a hydrogen atom in the alicyclic hydrocarbon group or the aromatic hydrocarbon group may be substituted with an alkyl group having 1 to 6 carbon atoms, an alkoxy group having 1 to 6 carbon atoms, a halogen atom, a cyano group, a nitro group, a —C≡C—$CH_3$ group, or a hydroxy group, m and n each independently represent an integer of 0 to 4 (m+n is an integer of 2 or more), $T^1$ represents —S—, —O—, —$CH_2$—, —NH—, —C(=O)—, —S(=O)—, or —C(=S)—, $T^2$ represents =$CR^2$— or =N—, and $R^2$ represents a hydrogen atom, a halogen atom, an alkyl group having 1 to 6 carbon atoms, an alkoxy group having 1 to 6 carbon atoms, a cyano group, a nitro group, or a hydroxy group].

According to a second aspect of the present invention, there is provided a composition containing the polymerizable compound according to the first aspect.

According to a third aspect of the present invention, there is provided a polymer obtained by polymerizing the composition according to the second aspect.

According to a fourth aspect of the present invention, there is provided an optically anisotropic body using the polymer according to the third aspect.

According to a fifth aspect of the present invention, there is provided a liquid crystal display device using the optically anisotropic body according to the fourth aspect.

According to a sixth aspect of the present invention, there is provided an organic EL device using the optically anisotropic body according to the fourth aspect.

Advantageous Effects of Invention

By using the polymerizable compound according to the present invention, an optically anisotropic body having excellent optical properties can be produced. Furthermore, a liquid crystal display device with an improved viewing angle can be produced.

DESCRIPTION OF EMBODIMENTS

Hereafter, the present invention will be described based on preferred embodiments, but is not limited to the embodiments.

<<Polymerizable Compound>>

A polymerizable compound according to a first embodiment of the present invention is a compound represented by general formula (1) below.

[Chem. 2]

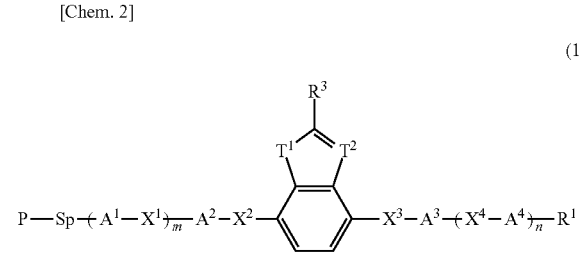

(1)

In the general formula (1), P represents a polymerizable functional group and Sp represents a spacer group or a single bond, $A^1$, $A^2$, $A^3$, and $A^4$ each independently represent a divalent alicyclic hydrocarbon group or aromatic hydrocarbon group, $X^1$, $X^2$, $X^3$, and $X^4$ each independently represent a divalent linking group or a single bond (at least one of $X^1$, $X^2$, $X^3$, and $X^4$ represents one of linking groups selected from —CH$_2$CH$_2$COO—, —CH$_2$CH$_2$OCO—, —COOCH$_2$CH$_2$—, —OCOCH$_2$CH$_2$—, —CH=CH—, —C≡C—, —CH—CHCOO—, —OCOCH=CH—, —N=N—, —C=N—, —N=C—, and —C=N—N=C—), $R^1$ represents an alkyl group having 1 to 12 carbon atoms, an alkoxy group having 1 to 12 carbon atoms, or "*-Sp-P" (* represents a bond with $A^4$ or $A^3$), $R^3$ represents an alkyl group having 1 to 6 carbon atoms, an alicyclic hydrocarbon group, or an aromatic hydrocarbon group, wherein a hydrogen atom in the alicyclic hydrocarbon group or the aromatic hydrocarbon group may be substituted with an alkyl group having 1 to 6 carbon atoms, an alkoxy group having 1 to 6 carbon atoms, a halogen atom, a cyano group, a nitro group, a —C≡C—CH$_3$ group, or a hydroxy group, m and n each independently represent an integer of 0 to 4 (m+n is an integer of 2 or more), $T^1$ represents —S—, —O—, —CH$_2$—, —NH—, —C(=O)—, —S(=O)—, or —C(=S)—, $T^2$ represents =CR$^2$— or =N—, and $R^2$ represents a hydrogen atom, a halogen atom, an alkyl group having 1 to 6 carbon atoms, an alkoxy group having 1 to 6 carbon atoms, a cyano group, a nitro group, or a hydroxy group.

The compound represented by the general formula (1) preferably has liquid crystallinity before polymerization. That is, the compound represented by the general formula (1) is preferably a polymerizable liquid crystal compound.

<Polymerizable Functional Group: P>

The polymerizable functional group represented by P in the general formula (1) may be any group used in known polymerizable liquid crystal compounds. Examples of the group include a vinyl group, a p-stilbene group, an acrylic group (acryloyl group), a methacrylic group (methacryloyl group), an acryloyloxy group, a methacryloyloxy group, a carboxy group, a methylcarbonyl group, a hydroxy group, an amide group, an alkylamino group having 1 to 4 carbon atoms, an amino group, an epoxy group, an oxetanyl group, an aldehyde group, an isocyanate group, and a thioisocyanate group.

The polymerizable functional group P is suitably a substituent selected from the group consisting of substituents represented by general formula (II-c), general formula (II-d), and general formula (II-e) below.

[Chem. 3]

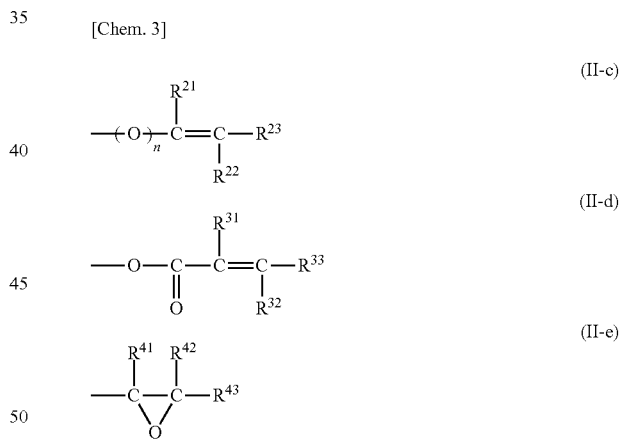

In the general formula (II-c), the general formula (II-d), and the general formula (II-e), $R^{21}$, $R^{22}$, $R^{23}$, $R^{32}$, $R^{33}$, $R^{41}$, $R^{42}$, and $R^{43}$ each independently represent a hydrogen atom, a halogen atom, or an alkyl group having 1 to 5 carbon atoms, and n represents 0 or 1. $R^{31}$ in the general formula (II-d) represents a hydrogen atom, a halogen atom, an alkyl group having 1 to 5 carbon atoms, or a halogenated alkyl group having 1 to 5 carbon atoms.

The polymerizable functional group represented by the above general formula bonds to Sp in the general formula (1) at its left end.

The alkyl group is preferably a linear or branched alkyl group and more preferably a linear alkyl group. Some or all of hydrogen atoms that bond to the alkyl group may be substituted with halogen atoms.

Among the polymerizable functional groups represented by the above general formulae, a group selected from the group consisting of groups represented by the general formula (II-c) and the general formula (II-d) is preferred, and a group selected from the group consisting of groups represented by the general formula (II-d) is further preferred from the viewpoint of improving polymerizability and storage stability.

Examples of the polymerizable functional group represented by the general formula (II-c), the general formula (II-d), or the general formula (II-e) include reactive functional groups (P-1) to (P-8) below. Among the reactive functional groups, (P-1) or (P-2) is preferred and (P-1) is further preferred from the viewpoint of improving the polymerizability and storage stability. Each of the polymerizable functional groups represented by (P-1) to (P-8) below bonds to Sp in the general formula (1) at its right end.

[Chem. 4]

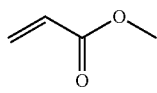
(P-1)

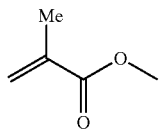
(P-2)

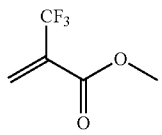
(P-3)

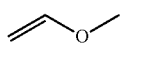
(P-5)

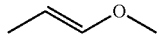
(P-6)

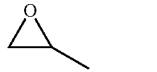
(P-7)

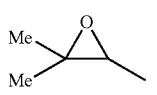
(P-8)

<Sp>

Sp in the general formula (1) represents a spacer group or a single bond. The spacer group is a divalent linking group capable of linking the polymerizable functional group P and $A^1$ or $A^2$, and is preferably a linking group that does not degrade the liquid crystallinity of the compound represented by the general formula (1) (may be called a compound (1) in this specification).

A suitable example of Sp is a linear alkylene group having 1 to 20 carbon atoms. One $CH_2$ group or two or more non-adjacent $CH_2$ groups present in the alkylene group may each independently be substituted with —O—, —S—, —NH—, —N($CH_3$)—, —CO—, —COO—, —OCO—, —OCOO—, —SCO—, —COS—, —CH=CH—, —C≡C— unless oxygen atoms, sulfur atoms, and an oxygen atom and a sulfur atom directly bond to each other. The number of carbon atoms of the alkylene group is preferably 2 to 10, more preferably 3 to 8, and further preferably 3 to 6 from the viewpoint of improving the liquid crystallinity.

<Cyclic Group: $A^1$, $A^2$, $A^3$, and $A^4$>

The cyclic groups $A^1$, $A^2$, $A^3$, and $A^4$ in the general formula (1) each independently represent a divalent alicyclic hydrocarbon group or aromatic hydrocarbon group. The cyclic group may be an aromatic heterocyclic group.

Examples of the cyclic group include a 1,4-phenylene group, a 1,4-cyclohexylene group, a 1,4-cyclohexenyl group, a tetrahydropyran-2,5-diyl group, a 1,3-dioxane-2,5-diyl group, a tetrahydrothiopyran-2,5-diyl group, a 1,4-bicyclo(2,2,2)octylene group, a decahydronaphthalene-2,6-diyl group, a pyridine-2,5-diyl group, a pyrimidine-2,5-diyl group, a pyrazine-2,5-diyl group, a 1,2,3,4-tetrahydronaphthalene-2,6-diyl group, a 2,6-naphthylene group, a phenanthrene-2,7-diyl group, a 9,10-dihydrophenanthrene-2,7-diyl group, a 1,2,3,4,4a,9,10a-octahydrophenanthrene2,7-diyl group, and a fluorene2,7-diyl group.

At least one hydrogen atom that bonds to the 1,4-phenylene group, the 1,4-cyclohexylene group, the 1,2,3,4-tetrahydronaphthalene-2,6-diyl group, the 2,6-naphthylene group, the phenanthrene-2,7-diyl group, the 9,10-dihydrophenanthrene-2,7-diyl group, the 1,2,3,4,4a,9,10a-octahydrophenanthrene2,7-diyl group, or the fluorene2,7-diyl group may be substituted with F, Cl, $CF_3$, $OCF_3$, a cyano group, an alkyl group having 1 to 8 carbon atoms, an alkoxy group having 1 to 8 carbon atoms, an alkanoyl group having 1 to 8 carbon atoms, an alkanoyloxy group having 1 to 8 carbon atoms, an alkenyl group having 2 to 8 carbon atoms, an alkenyloxy group having 2 to 8 carbon atoms, an alkenoyl group having 2 to 8 carbon atoms, or an alkenoyloxy group having 2 to 8 carbon atoms.

The cyclic groups $A^1$, $A^2$, $A^3$, and $A^4$ in the general formula (1) preferably each independently represent the above-mentioned 1,4-phenylene group or 1,4-cyclohexylene group. Use of such a cyclic group improves the liquid crystallinity of the polymerizable compound according to this embodiment and easily improves the alignment of the resulting polymer.

<Linking Group or Single Bond: $X^1$, $X^2$, $X^3$, and $X^4$>

$X^1$, $X^2$, $X^3$, and $X^4$ in the general formula (1) each independently represent a divalent linking group or a single bond.

Preferred examples of $X^1$, $X^2$, $X^3$, and $X^4$ each independently include —$(CH_2)_u$—O—COO—, —$(CH_2)_u$—OCO—, —$(CH_2)_u$—COO—, —$(CH_2)_u$—O—, —O—COO—$(CH_2)_u$—, —OCO—$(CH_2)_u$—, —COO—$(CH_2)_u$—, —O—$(CH_2)_u$—, —CH=CH—, —C≡C—, —CH=CHCOO—, —OCOCH=CH—, —N=N—, —C=N—, —N=C—, —C=N—N=C—, —$CH_2CH_2$—, and a single bond. Herein, u represents an integer of 0 to 2. When u represents 0, —$(CH)_u$—O—COO— and —O—COO—$(CH_2)_u$— indicate —O—COO—, —$(CH_2)_u$—O— and —O—$(CH_2)_u$— indicate —O—, —$(CH_2)_u$—COO— and —COO—$(CH_2)_u$— indicate —COO—, and —$(CH_2)_u$—OCO— and —OCO—$(CH_2)_u$— indicate —OCO—.

$X^2$ and $X^3$ preferably each independently represent —$CH_2CH_2$—, a single bond, —CH=CH—, —C≡C—, —CH=CHCOO—, —OCO—CH=CH—, —$(CH_2)_u$—O—COO—, —$(CH_2)_u$—OCO—, —$(CH_2)_u$—COO—, —$(CH_2)_u$—O—, —O—COO—$(CH_2)_u$—, —OCO—$(CH_2)_u$—, —COO—$(CH_2)_u$—, or —O—$(CH_2)_u$—. Herein, u represents an integer of 0 to 2. When u represents 0, —$(CH_2)_u$—COO— and —COO—$(CH_2)_u$— indicate —COO—, and —$(CH_2)_u$—OCO— and —OCO—$(CH_2)_u$— indicate —OCO—.

At least one of $X^2$ and $X^3$ is preferably one of linking groups selected from —$CH_2CH_2COO$—, —$CH_2CH_2OCO$—, —$COOCH_2CH_2$—, —$OCOCH_2CH_2$—, —$CH=CH$—, —$C\equiv C$—, —$CH=CHCOO$—, —$OCOCH=CH$—, —$N=N$—, —$C=N$—, —$N=C$—, and —$C=N-N=C$—.

When at least one of $X^2$ and $X^3$ represents the preferred linking group described above, the alignment of a polymer formed of the polymerizable compound according to this embodiment is easily improved without degrading the liquid crystallinity of the polymerizable compound. It is believed that the alignment is improved by introducing the above linking group, which is relatively flexible, into both sides of a bulky moiety (vertical unit) extending in a direction vertical to the major axis of the molecule. One of the reasons for which the alignment is improved is that the solubility of the polymerizable compound in a solvent is improved by introducing the above linking group.

Preferred combinations of $X^2$ and $X^3$ are exemplified below with the expression of "$X^2/X^3$":

"—$COO$—$(CH_2)_u$—/—$CH_2CH_2$—$COO$—", "—$COO$—$(CH_2)_u$—/—$COO$—$CH_2CH_2$—",
"—$COO$—$(CH_2)_u$—/—$OCO$—$CH_2CH_2$—", "—$COO$—$(CH_2)_u$—/—$CH_2CH_2$—$OCO$—",
"—$OCO$—$(CH_2)_u$—/—$CH_2CH_2$—$COO$—", "—$OCO$—$(CH_2)_u$—/—$COO$—$CH_2CH_2$—",
"—$OCO$—$(CH_2)_u$—/—$OCO$—$CH_2CH_2$—", "—$OCO$—$(CH_2)_u$—/—$CH_2CH_2$—$OCO$—",
"—$OCO$—$CH_2CH_2$—/—$COO$—$(CH_2)_u$—",
"—$CH_2CH_2$—$OCO$—/—$COO$—$(CH_2)_u$—",
"—$CH_2CH_2$—$COO$—/—$COO$—$(CH_2)_u$—", "—$COO$—$CH_2CH_2$—/—$COO$—$(CH_2)_u$—",
"—$OCO$—$CH_2CH_2$—/—$OCO$—$(CH_2)_u$—",
"—$CH_2CH_2$—$OCO$—/—$OCO$—$(CH_2)_u$—",
"—$CH_2CH_2$—$COO$—/—$OCO$—$(CH_2)_u$—", "—$COO$—$CH_2CH_2$—/—$OCO$—$(CH_2)_u$—", (u represents an integer of 0 to 2)

"single bond/—$CH_2CH_2$—$COO$—", "single bond/—$COO$—$CH_2CH_2$—",
"single bond/—$OCO$—$CH_2CH_2$—", "single bond/—$CH_2CH_2$—$OCO$—",
"—$OCO$—$CH_2CH_2$—/single bond", "—$CH_2CH_2$—$OCO$—/single bond",
"—$CH_2CH_2$—$COO$—/single bond", and "—$COO$—$CH_2CH_2$—/single bond".

More preferred combinations of $X^2$ and $X^3$ are exemplified below with the expression of "$X^2/X^3$":

"—$OCO$—$CH_2CH_2$—/—$CH_2CH_2$—$COO$—",
"—$CH_2CH_2$—$OCO$—/—$COO$—$CH_2CH_2$—",
"—$CH_2CH_2$—$COO$—/—$OCO$—$CH_2CH_2$—", "—$COO$—$CH_2CH_2$—/—$CH_2CH_2$—$OCO$—",
"—$O$—$CH_2CH_2$—/—$CH_2CH_2$—$O$—", "—$CH_2CH_2$—$O$—/—$O$—$CH_2CH_2$—",
"—$COO$—$CH_2CH_2$—$CO$—", "—$COO$—/—$COO$—$CH_2CH_2$—",
"—$COO$—/—$OCO$—$CH_2CH_2$—", "—$COO$—/—$CH_2CH_2$—$OCO$—",
"—$OCO$—/—$CH_2CH_2$—$COO$—", "—$OCO$—/—$COO$—$CH_2CH_2$—",
"—$OCO$—/—$OCO$—$CH_2CH_2$—", "—$OCO$—/—$CH_2CH_2$—$OCO$—",
"—$OCO$—$CH_2CH_2$—/—$COO$—", "—$CH_2CH_2$—$OCO$—/—$COO$—",
"—$CH_2CH_2$—$COO$—/—$COO$—", "—$COO$—$CH_2CH_2$—/—$COO$—",
"—$OCO$—$CH_2CH_2$—/—$OCO$—", "—$CH_2CH_2$—$OCO$—/—$OCO$—",
"—$CH_2CH_2$—$COO$—/—$OCO$—", "—$COO$—$CH_2CH_2$—/—$OCO$—",
"single bond/—$CH_2CH_2$—$COO$—", "single bond/—$COO$—$CH_2CH_2$—",
"single bond/—$OCO$—$CH_2CH_2$—", "single bond/—$CH_2CH_2$—$OCO$—",
"—$OCO$—$CH_2CH_2$—/single bond", "—$CH_2CH_2$—$OCO$—/single bond",
"—$CH_2CH_2$—$COO$—/single bond", "—$COO$—$CH_2CH_2$—/single bond",
"—$CH_2CH_2$—/—$CH_2CH_2$—$COO$—", "—$CH_2CH_2$—/—$COO$—$CH_2CH_2$—",
"—$CH_2CH_2$—/—$OCO$—$CH_2CH_2$—", and "—$CH_2CH_2$—/—$CH_2CH_2$—$OCO$—".

Further preferred combinations of $X^2$ and $X^3$ are exemplified below with the expression of "$X^2/X^3$":

"—$OCO$—$CH_2CH_2$—/—$CH_2CH_2$—$COO$—",
"—$CH_2CH_2$—$OCO$—/—$COO$—$CH_2CH_2$—",
"—$O$—$CH_2CH_2$—/—$CH_2CH_2$—$O$—", "—$CH_2CH_2$—$O$—/—$O$—$CH_2CH_2$—",
"—$COO$—/—$CH_2CH_2$—$COO$—", "—$COO$—/—$COO$—$CH_2CH_2$—",
"—$OCO$—/—$CH_2CH_2$—$COO$—", "—$CO$—/—$COO$—$CH_2CH_2$—",
"—$OCO$—$CH_2CH_2$—/—$COO$—", "—$CH_2CH_2$—$OCO$—/—$COO$—",
"—$OCO$—$CH_2CH_2$—/—$OCO$)—", "—$CH_2CH_2$—$OCO$—/—$OCO$—",
"single bond/—$CH_2CH_2$—$COO$—", "single bond/—$COO$—$CH_2CH_2$—",
"—$OCO$—$CH_2CH_2$—/single bond", "—$CH_2CH_2$—$OCO$—/single bond",
"—$CH_2CH_2$—/—$CH_2CH_2$—$COO$—", "—$CH_2CH_2$—/—$COO$—$CH_2CH_2$—",
"—$COO$—$CH_2CH_2$—/—$OCO$—", and "—$COO$—$CH_2CH_2$—/—$CH_2CH_2$—$OCO$—".

The compounds represented by the general formula (1) and having the further preferred combinations of $X^2$ and $X^3$ are represented by general formulae (1-a) to (1-t) below.

[Chem. 5]

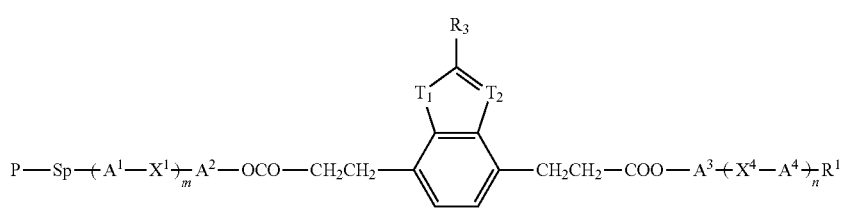

(1-a)

-continued
(1-b)
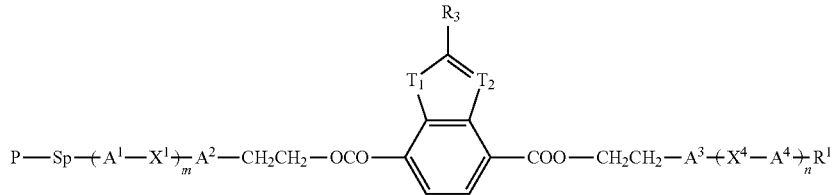
(1-c)
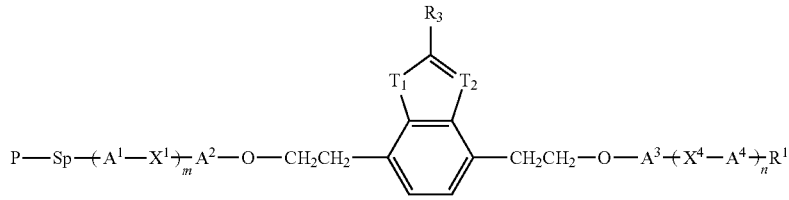
(1-d)
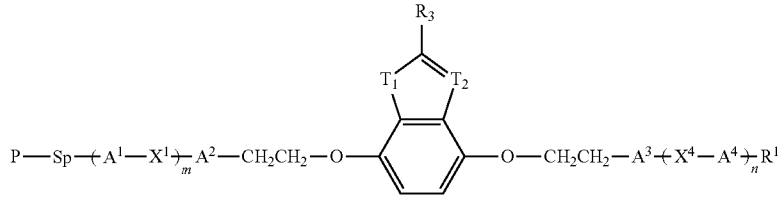
(1-e)
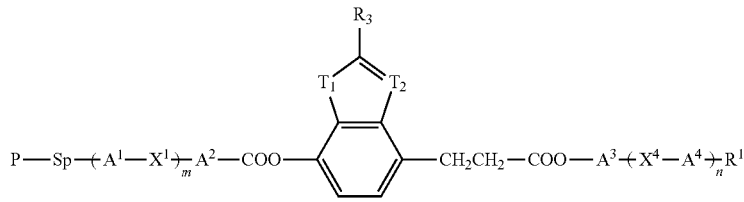
(1-f)
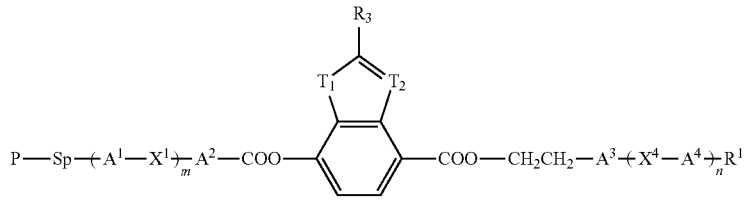
[Chem. 6]
(1-g)
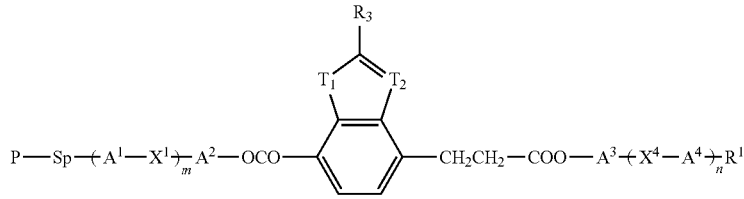
(1-h)
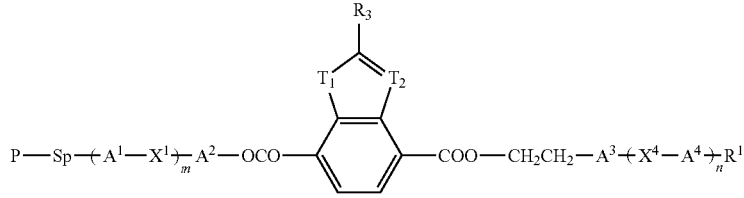

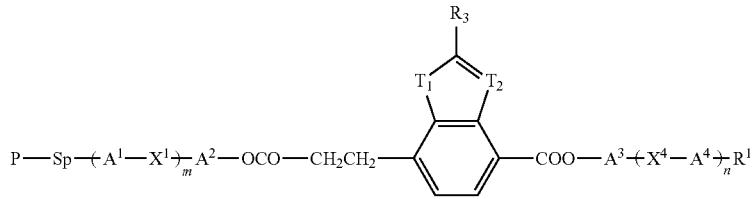
(1-i)
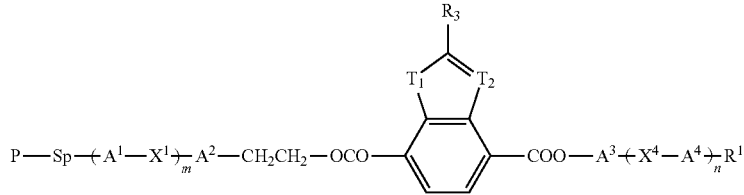
(1-j)
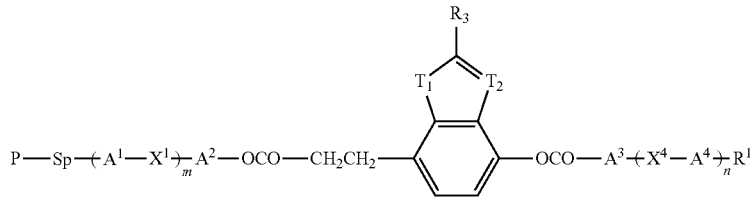
(1-k)
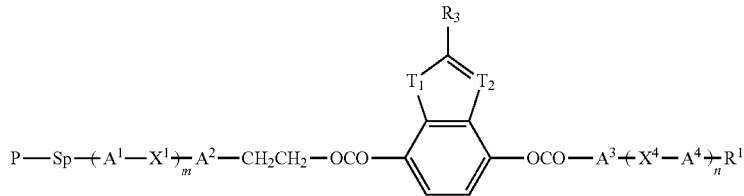
(1-l)
[Chem. 7]
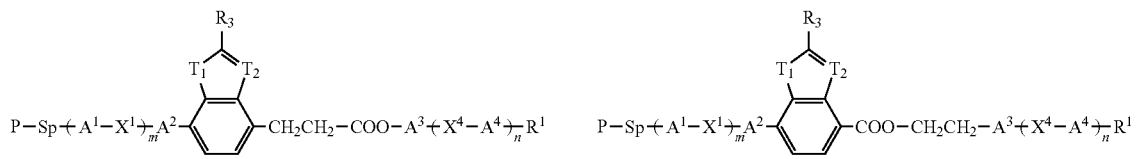
(1-m)     (1-n)
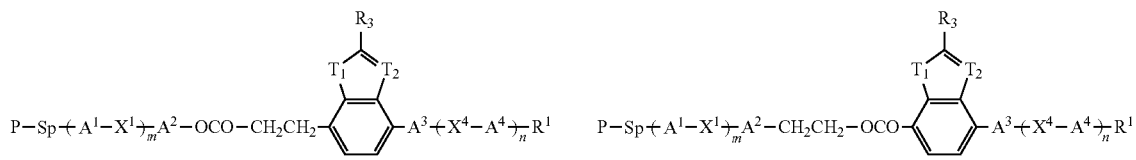
(1-o)     (1-p)
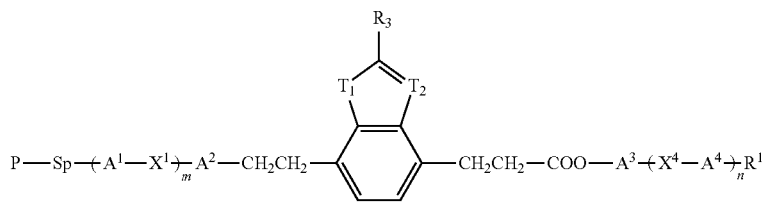
(1-q)

-continued

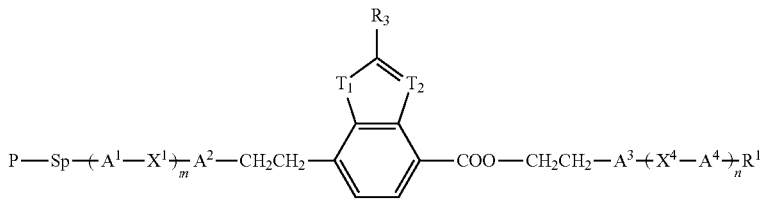

(1-r)

[Chem. 8]

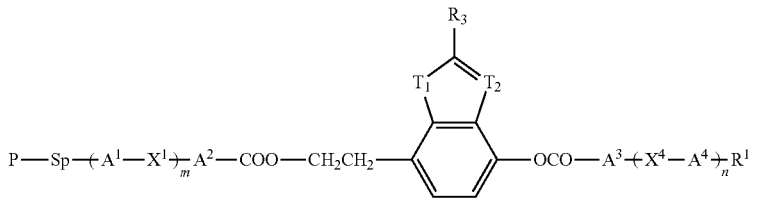

(1-s)

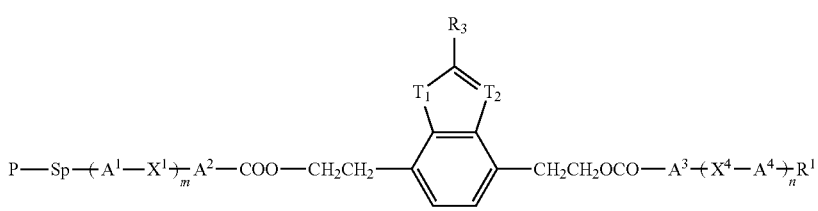

(1-t)

$X^1$ and $X^4$ in the general formula (1) preferably each independently represent —COO—, —OCO—, —CH$_2$CH$_2$—, a single bond, —CH═CH—, —C≡C—, —CH$_2$O—, or —OCH$_2$— and more preferably each independently represent —COO—, —OCO—, or —CH$_2$CH—.

Each of the linking groups $X^1$ and $X^4$ exemplified herein can be freely combined with the preferred combinations of X and $X^3$ described above.

<m and n>

In the general formula (1), m and n each independently represent an integer of 0 to 4, and m+n is an integer of 2 or more.

From the viewpoint of improving the liquid crystallinity of the polymerizable compound according to this embodiment, m and n preferably each independently represent 0 to 3, more preferably each independently represent 0 to 2, and further preferably each independently represent 1 or 2. Furthermore, m and n are preferably the same integer.

<End Group: $R^1$>

The end group $R^1$ in the general formula (1) represents an alkyl group having 1 to 12 carbon atoms, an alkoxy group having 1 to 12 carbon atoms, or "*-Sp-P". Herein, "*" indicates a bond with $A^4$ when n represents an integer of 1 or more or a bond with $A^3$ when n represents 0.

Sp and the polymerizable functional group P in "*-Sp-P" are the same as those described above. When two Sp are present in a molecule, they may be the same or different and are preferably the same. When two P are present in a molecule, they may be the same or different and are preferably the same.

The alkyl group may be any of a linear alkyl group, a branched alkyl group, and a cyclic alkyl group, is preferably a linear alkyl group or a branched alkyl group, and more preferably a linear alkyl group. The number of carbon atoms of the alkyl group is preferably 2 to 10, more preferably 3 to 8, and further preferably 3 to 6.

An example of an alkyl group constituting the alkoxy group is the same alkyl group described above. The number of carbon atoms of the alkyl group constituting the alkoxy group is preferably 1 to 8, more preferably 1 to 6, and further preferably 1 to 3.

The end group $R^1$ is preferably "*-Sp-P" from the viewpoint of improving the liquid crystallinity and alignment of the polymerizable compound according to this embodiment and also improving the optical properties of an optically anisotropic body such as a retardation film that uses the polymerizable compound. In this preferred case, two Sp present in a molecule may be the same or different and are preferably the same. Two P present in a molecule may be the same or different and are preferably the same.

<$T^1$ and $T^2$>

In the general formula (1), $T^1$ represents —S—, —O—, —CH$_2$—, —NH—, —C(═O)—, —S(═O)—, or —C(═S)—, preferably represents —NH— or —S—, and more preferably represents —S—.

In the general formula (1), $T^2$ represents "═CR$^2$—" or "═N—" and $R^2$ represents a hydrogen atom, a halogen atom, an alkyl group having 1 to 6 carbon atoms, an alkoxy group having 1 to 6 carbon atoms, a cyano group, a nitro group, or a hydroxy group. Note that "═CR$^2$—" refers to "═C(—R$^2$)—", and thus a hydrogen atom does not bond to the carbon atom C to which $R^2$ bonds.

In the general formula (1), $T^2$ preferably represents ═CH—, ═C(—CH$_3$)—, ═C(—OCH$_3$)—, or ═N— and more preferably represents ═N—.

When $R^2$ represents an alkyl group or an alkoxy group, examples of the alkyl group of $R^2$ and an alkyl group constituting the alkoxy group of $R^2$ include a methyl group, an ethyl group, a propyl group, an isopropyl group, a butyl group, an isobutyl group, a sec-butyl group, a tert-butyl group, a pentyl group, and a hexyl group. The number of carbon atoms of the alkyl group is preferably 1 to 4, more preferably 1 or 2, and further preferably 1.

When $R^2$ represents a halogen atom, $R^2$ preferably represents a fluorine atom or a chlorine atom.

The preferred combinations of $T^1$ and $T^2$ are shown using general formulae (2-1) to (2-5) below.

[Chem. 9]

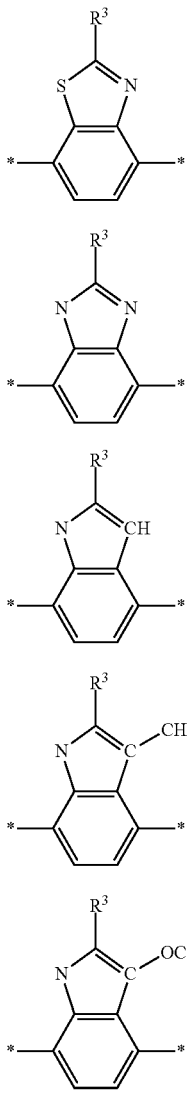

(2-1)

(2-2)

(2-3)

(2-4)

(2-5)

[In the formulae, "*" indicate bonds with $X^2$ and $X^3$ in the general formula (1), and $R^3$ is the same as $R^3$ in the general formula (1).]

The combinations of $T^1$ and $T^2$ exemplified herein can be freely combined with the above-described preferred combinations of $X^2$ and $X^3$.

<$R^3$>

In the general formula (1), $R^3$ represents an alkyl group having 1 to 6 carbon atoms, an alicyclic hydrocarbon group, or an aromatic hydrocarbon group. In particular, $R^3$ preferably represents an alicyclic hydrocarbon group or an aromatic hydrocarbon group and more preferably represents an aromatic hydrocarbon group from the viewpoint of improving the liquid crystallinity and optical properties.

A hydrogen atom in the alicyclic hydrocarbon group and the aromatic hydrocarbon group may be substituted with an alkyl group having 1 to 6 carbon atoms, an alkoxy group having 1 to 6 carbon atoms, a halogen atom, a cyano group, a nitro group, a —C≡C—CH$_3$ group, or a hydroxy group. Among the substituents, a nitro group, a cyano group, and a —C≡C—CH$_3$ group are preferred from the viewpoint of improving the liquid crystallinity and alignment of the polymerizable compound.

Examples of the alkyl group and an alkyl group constituting the alkoxy group include a methyl group, an ethyl group, a propyl group, an isopropyl group, a butyl group, an isobutyl group, a sec-butyl group, a tert-butyl group, a pentyl group, and a hexyl group. The number of carbon atoms of the alkyl group is preferably 1 to 4, more preferably 1 or 2, and further preferably 1.

The number of carbon atoms of the alicyclic hydrocarbon group is preferably 4 to 10 and more preferably 5 to 8. Examples of the alicyclic hydrocarbon group include groups represented by formulae (3-1) to (3-4) below. Some of carbon atoms constituting the alicyclic hydrocarbon group may be substituted with heteroatoms such as a nitrogen atom, an oxygen atom, and a sulfur atom. Examples of such an alicyclic group include groups represented by formulae (3-5) to (3-10) below. In the formulae, "*" indicates a bond with a carbon atom to which $R^3$ in the formula (1) bonds.

[Chem. 10]

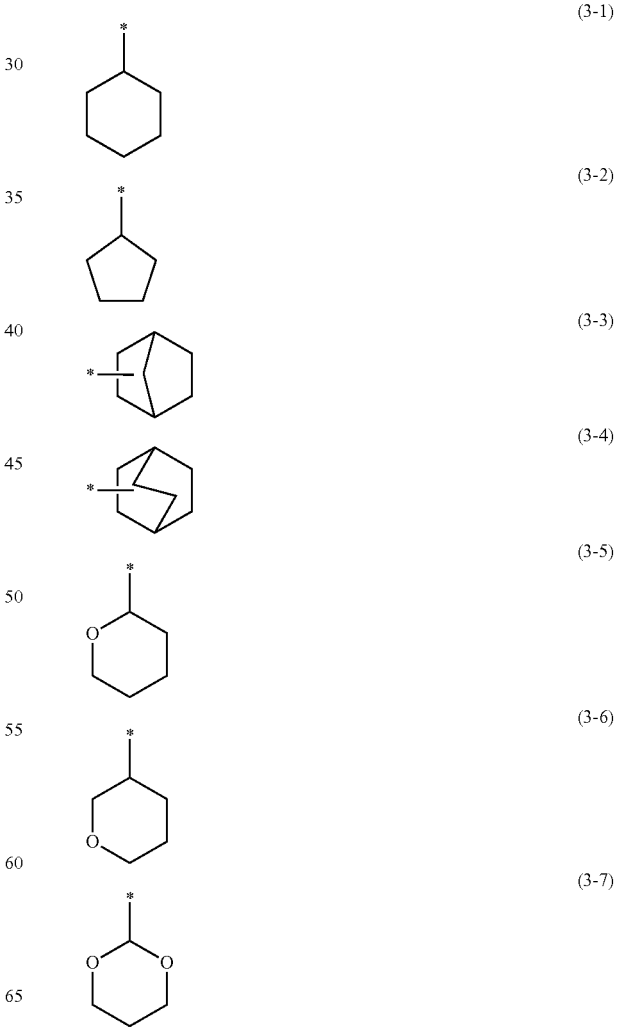

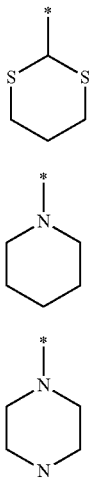

(3-8)

(3-9)

(3-10)

Among the groups (3-1) to (3-10), the group (3-1) or (3-2) is preferred. The groups (3-1) and (3-2) may have the above-described substituent. The substituent is preferably a nitro group, a cyano group, or a —C≡C—CH$_3$ group. The substituent preferably bonds to a 4-position of the group (3-1) or a 3-position of the group (3-2). Herein, a carbon atom that bonds to "*" among carbon atoms constituting the ring is a 1-position carbon atom.

The number of carbon atoms of the aromatic hydrocarbon group is preferably 6 to 20 and more preferably 6 to 14. Examples of the aromatic hydrocarbon group include groups represented by formulae (4-1) to (4-4) below. In the formulae, "*" indicates a bond with a carbon atom to which R in the general formula (1) bonds.

[Chem. 11]

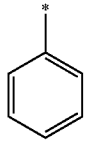

(4-1)

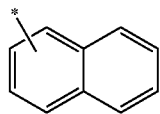

(4-2)

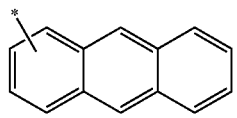

(4-3)

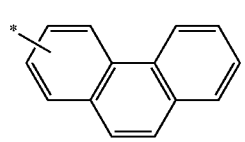

(4-4)

Among the groups (4-1) to (4-4), the group (4-1) or (4-2), that is, a phenyl group or a naphthyl group is preferred and a phenyl group is further preferred. The phenyl group preferably has the above-described substituent. The substituent is preferably a nitro group, a cyano group, or a —C≡C—CH— group. The substituent preferably bonds to a 4-position of the phenyl group. Herein, a carbon atom that bonds to "*" among carbon atoms constituting the aromatic ring is a 1-position carbon atom.

$R^3$ exemplified above can be freely combined with the preferred combinations of $T^1$ and $T^2$ and the preferred combinations of $X^2$ and $X^3$.

<<Composition>>

A composition according to a second embodiment of the present invention contains the polymerizable compound according to the first embodiment. The composition according to this embodiment may contain only one of the polymerizable compounds represented by the general formula (1) or two or more of the polymerizable compounds. Normally, the composition preferably contains 1 to 4 of the polymerizable compounds, more preferably 1 to 3 of the polymerizable compounds, and further preferably 1 or 2 of the polymerizable compounds.

The composition according to this embodiment may contain a publicly known polymerizable compound, in addition to the polymerizable compound according to the first embodiment. Examples of the publicly known polymerizable compound include polymerizable compounds represented by general formulae (A1) to (A24) below.

[Chem. 12]

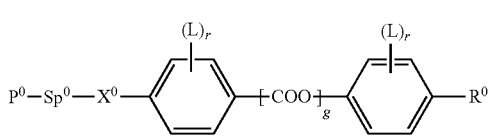

(A1)

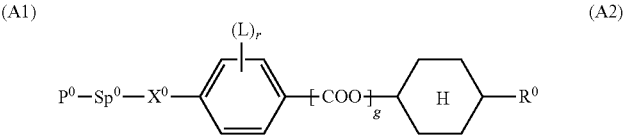

(A2)

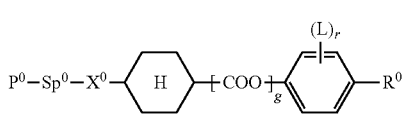

(A3)

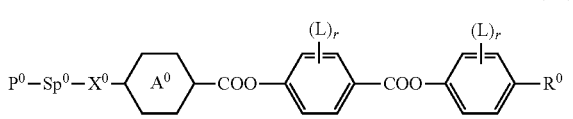

(A4)

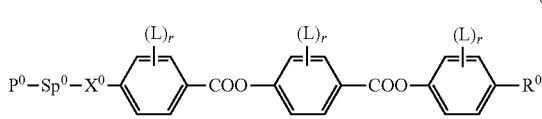

(A5)

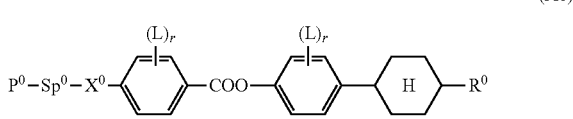

(A6)

(A7) 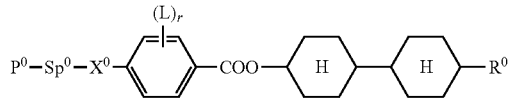
(A8) 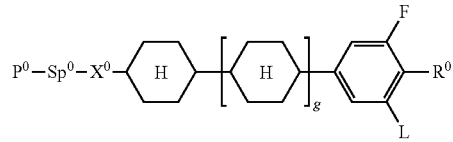
(A9) 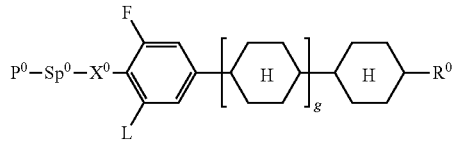
(A10) 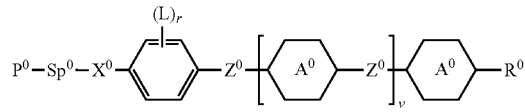
[Chem. 13]
(A11) 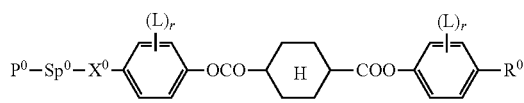
(A12) 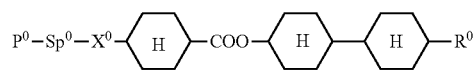
(A13) 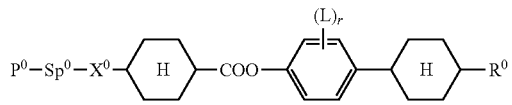
(A14) 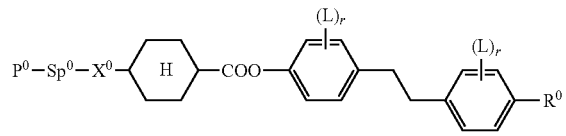
(A15) 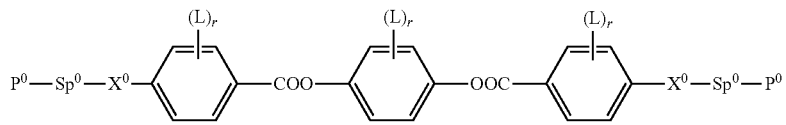
(A16) 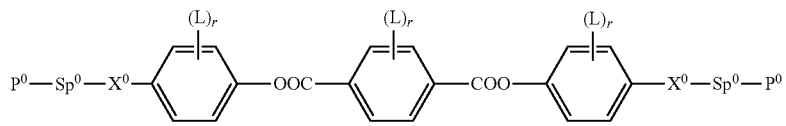
(A17) 
(A18) 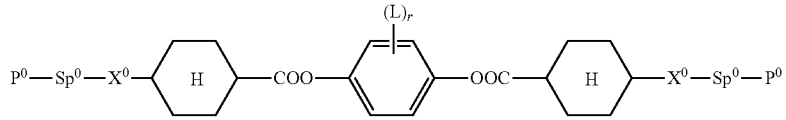
(A19) 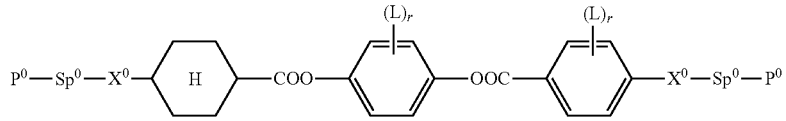
(A20) 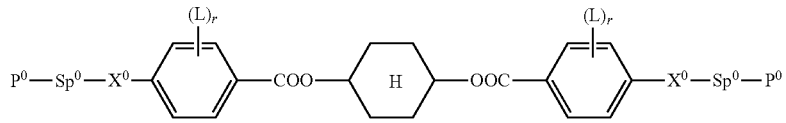
[Chem. 14]
(A21) 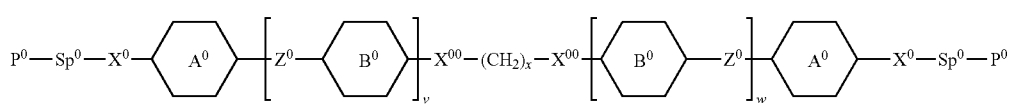

-continued

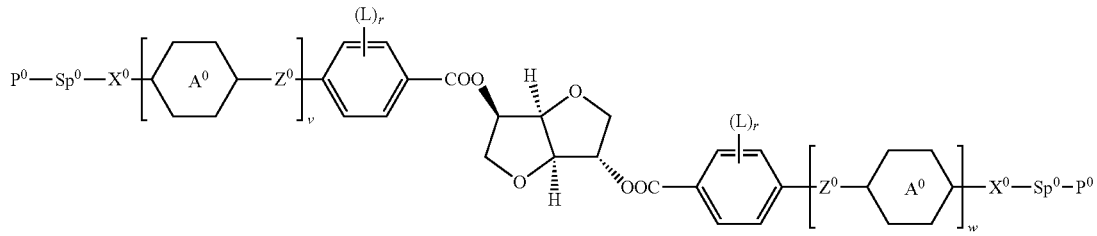
(A22)

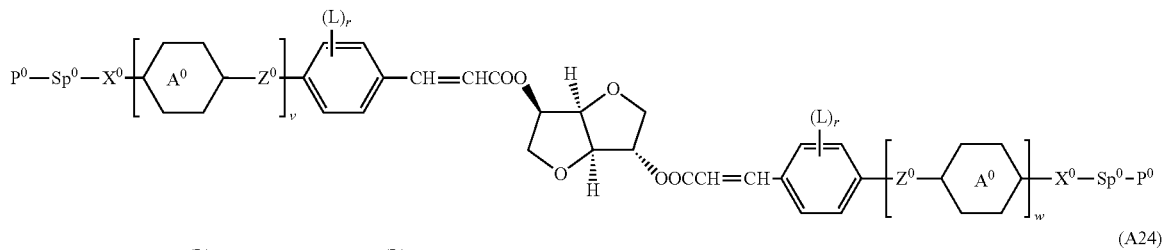
(A23)

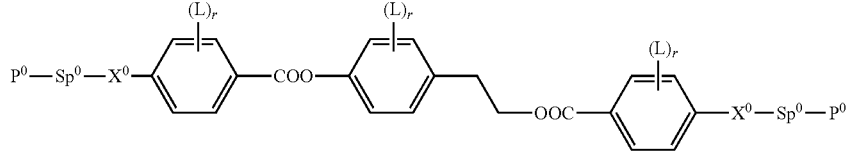
(A24)

In the general formulae (A1) to (A24), $P^0$ represents a polymerizable group having one of meanings given to P described above, and when a plurality of $P^0$ are present, $P^0$ each independently represent a polymerizable group having one of meanings given to P. $P^0$ preferably represents acryl, methacryl, oxetane, 3-ethyloxetane, epoxy, vinyloxy, or a styrene group. $Sp^0$ represents a spacer group having one of meanings given to Sp described above or a single bond.

$X^0$ represents —O—, —S—, —CO—, —COO—, —OCO—, —O—COO—, —CO—NR$^0$—, —NR$^0$—CO—, —NR$^0$—CO—NR$^9$—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^6$—, —CY$^1$=CY$^2$—, —C≡C—, —CH=CH—COO—, —OCO—CH=CH—, or a single bond, $Sp^0$-$X^0$ is preferably selected from —(CH$_2$)$_{p1}$—, —(CH$_2$)$_{p1}$—O—, —(CH$_2$)$_{p1}$—CO—O—, and —(CH$_2$)$_{p1}$—O—CO—O—. Herein, p1 represents an integer of 1 to 12. When such a group has an oxygen atom, the group bonds to the adjacent ring through the oxygen atom, $A^0$ and $B^0$ are each represent 1,4-phenylene (this may be substituted with one, two, three, or four groups L) or trans-1,4-cyclohexylene and, when a plurality of $A^0$ and $B^0$ are present, $A^0$ and $B^0$ are each independently represent 1,4-phenylene or trans-1,4-cyclohexylene, H represents trans-1,4-cyclohexylene, $Z^0$ represents —COO—, —OCO—, —CH$_2$CH$_2$—, —C≡C—, —CH=CH—, —CH=CH—COO—, —OCO—CH=CH—, or a single bond and, when a plurality of $Z^0$ are present, $Z^0$ each independently represent —COO—, —OCO—, —CH$_2$CH$_2$—, —C≡C—, —CH=CH—, —CH=CH—COO—, —OCO—CH=CH—, or a single bond.

$R^0$ represents alkyl, alkoxy, thioalkyl, alkylcarbonyl, alkoxycarbonyl, alkylcarbonyloxy, or alkoxycarbonyloxy having 1 to 20 carbon atoms and preferably 1 to 15 carbon atoms (this group may be fluorinated), or $Y^0$ or P-$Sp^0$-$X^0$—, $Y^0$ represents F, Cl, CN, NO$_2$, OCH$_3$, OCN, SCN, or SF$_5$; alkylcarbonyl, alkoxycarbonyl, alkylcarbonyloxy, or alkoxycarbonyloxy that has 1 to 4 carbon atoms and may be fluorinated; or alkyl or alkoxy that has 1 to 4 carbon atoms and that is monofluorinated, oligofluorinated, or polyfluorinated, $X^{00}$ represents —O—, —S—, —CO—, —COO—, —OCO—, —O—COO—, —CO—NR$^{01}$—, —NR$^{01}$—CO—, —NR$^{01}$—CO—NR$^{01}$—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^{01}$—, —CF=CF—, —C≡C—, —CH=CH—COO—, —OCO—CH=CH—, or a single bond, $R^{01}$ represents H or alkyl having 1 to 12 carbon atoms, L represents F, Cl, CN, SCN, or SF$_5$; linear or branched alkyl, alkoxy, alkenyl, alkynyl, alkylcarbonyl, alkoxycarbonyl, alkylcarbonyloxy, or alkoxycarbonyloxy (herein, groups other than alkyl and alkoxy have at least two carbon atoms and branched groups have at least three carbon atoms) that has 1 to 12 carbon atoms and may be monofluorinated or polyfluorinated; or alkyl, alkoxy, alkylcarbonyl, alkoxycarbonyl, alkylcarbonyloxy, or alkoxycarbonyloxy that has 1 to 5 carbon atoms and may be halogenated, and when a plurality of L are present, L may be the same or different, r represents 0, 1, 2, 3, or 4, g represents 0 or 1, and v and w each independently represent 0, 1, or 2, wherein the benzene ring and the naphthalene ring may be additionally substituted with at least one of the same group L or different groups L.

In the general formulae (A1) to (A24), "—OOC—" means "—O—C(=O)—", which is the same as "—OCO—".

When the total weight of the polymerizable compound contained in the composition according to this embodiment is assumed to be 100 parts by weight, the total content of the polymerizable compounds represented by the general formula (1) is preferably 10 to 100 parts by weight, more preferably 30 to 100 parts by weight, and further preferably 50 to 100 parts by weight.

The composition according to this embodiment preferably contains a bifunctional compound that intramolecularly has two polymerizable functional groups. When the composition containing a bifunctional compound is used for polymer substrates and laminates thereof, excellent alignment, optical properties, and the like can be imparted.

Specific examples of the use include optically anisotropic bodies such as retardation films, patterned retardation films, and homogeneously aligned (horizontally aligned) liquid crystal films in the field of liquid crystal displays.

The substrate to which a solution containing the composition according to this embodiment is applied is not particularly limited as long as the substrate is a substrate that is typically used for liquid crystal devices, displays, optical components, and optical films and that is made of a material having resistance to heating during drying after the application of the composition according to this embodiment or during the production of the liquid crystal device. Examples of the substrate include glass substrates, metal substrates, ceramic substrates, and polymer substrates made of an organic material. In particular, the polymer substrate is preferred because the polymer substrate can be produced by roll to roll and is more easily handled than glass substrates or the like. Furthermore, a substrate made of a polymer compound (polymer substrate) has a high affinity for the polymerizable compound according to the first embodiment, and thus excellent alignment is easily achieved after a solution containing the polymerizable compound is applied onto the polymer substrate and dried. Therefore, the polymerizable compound according to this embodiment is suitable for use in stacking on the polymer substrate.

Preferred examples of the polymer compound for the polymer substrate include cellulose derivatives, polyolefins, polyesters, polyethylene terephthalate, polycarbonate, polyacrylates, polyarylate, polyethersulfone, polyimide, polyphenylene sulfide, polyphenylene ether, nylon, and polystyrene. In particular, cycloolefin polymer, cellulose triacetate, and poly(methyl methacrylate) resin are preferred.

The substrate may be subjected to an alignment treatment so that the polymerizable compound is easily aligned when the composition according to this embodiment is applied and dried. The alignment treatment may be performed by a method in which a substrate is directly subjected to a rubbing treatment or a method in which an alignment film used for typical liquid crystal devices is applied onto a substrate and then a rubbing treatment is performed. A particularly preferred method is a publicly known method that uses a photo-alignment film. Use of the photo-alignment film allows the production of patterned retardation films.

<Organic Solvent>

An organic solvent for the composition according to this embodiment is not particularly limited as long as the polymerizable compound represented by the general formula (1) can be dissolved in the organic solvent. The organic solvent is preferably a solvent that allows drying of the composition through volatilization of the solvent at 100° C. or lower and that does not erode the substrate used. Examples of the solvent include aromatic hydrocarbons such as toluene, xylene, cumene, and mesitylene; ester solvents such as methyl acetate, ethyl acetate, propyl acetate, and butyl acetate; ketone solvents such as methyl ethyl ketone, methyl isobutyl ketone, cyclohexanone, and cyclopentanone; ether solvents such as tetrahydrofuran, 1,2-dimethoxyethane, and anisole; amide solvents such as N,N-dimethylformamide and N-methyl-2-pyrrolidone; and propylene glycol monomethyl ether acetate, diethylene glycol monomethyl ether acetate, γ-butyrolactone, chlorobenzene, and chloroform. These organic solvents may be used alone or in combination of two or more as a mixture.

Among the exemplified organic solvents, chloroform, toluene, ethyl acetate, methyl ethyl ketone, methyl isobutyl ketone, cyclohexanone, cyclopentanone, propylene glycol monomethyl ether acetate, and N-methyl-2-pyrrolidone are further preferred because they dissolve the polymerizable compound represented by the general formula (1) well, provide excellent alignment of a film formed by polymerizing the composition, and provide ease of drying at 100° C. or lower.

The content of the organic solvent relative to the total weight of the composition according to this embodiment may be controlled to such a value that the composition is easily applied onto a substrate. The content is, for example, preferably 40 to 90 wt % and more preferably 50 to 80 wt %.

<Polymerization Initiator>

The composition according to this embodiment preferably contains at least one polymerization initiator.

A polymerization initiator is a compound effective for efficiently polymerizing the polymerizable compound according to the first embodiment. The polymerization initiator is preferably a photopolymerization initiator. Specifically, the polymerization initiator is preferably the following compounds: Irgacure 651, Irgacure 184, Irgacure 907, Irgacure 127, Irgacure 369, Irgacure 379, Irgacure 819, Irgacure OXE01, Irgacure OXE02, Lucirin TPO, and DAROCUR 1173 manufactured by BASF; and Esacure 1001M, Esacure KIP150, Speedcure BEM, Speedcure BMS, Speedcure PBZ, and benzophenone manufactured by LAMBSON.

These polymerization initiators may be used alone or in combination of two or more. A sensitizer or the like may be further added.

The content of the polymerization initiator relative to the total weight of the solid content of the composition according to this embodiment is, for example, preferably 0.1 to 10 wt %, more preferably 1.0 to 7.0 wt %, and further preferably 3.0 to 6.0 wt %.

<Surfactant, Etc.>

The composition according to this embodiment preferably contains a surfactant or a compound having a repeating unit represented by general formula (VI) below and having a weight-average molecular weight of 100 or more.

[Chem. 15]

$$\pmb{+}\mathrm{CR}^{11}\mathrm{R}^{12}\mathrm{-CR}^{13}\mathrm{R}^{14}\pmb{+}\qquad(v)$$

[In the formula, $R^{11}$, $R^{12}$, $R^{13}$, and $R^{14}$ each independently represent a hydrogen atom, a halogen atom, or a hydrocarbon group having 1 to 20 carbon atoms. At least one hydrogen atom in the hydrocarbon group may be substituted with a halogen atom.]

The surfactant and the compound represented by the general formula (VI) impart an effect of decreasing the tilt angle of a liquid crystal compound at an interface with air. Examples of the surfactant include alkyl carboxylates, alkyl phosphates, alkyl sulfonates, fluoroalkyl carboxylates, fluoroalkyl phosphates, fluoroalkyl sulfonates, polyoxyethylene derivatives, fluoroalkyl ethylene oxide derivatives, polyethylene glycol derivatives, alkylammonium salts, fluoroalkylammonium salts, and silicone derivatives. Among them, a fluorine-containing surfactant and a silicone derivative are particularly preferred.

Specific examples of the surfactant include "MEGAFAC F-110", "MEGAFAC F-113", "MEGAFAC F-120", "MEGAFAC F-812", "MEGAFAC F-142D", "MEGAFAC F-144D", "MEGAFAC F-150", "MEGAFAC F-171", "MEGAFAC F-173", "MEGAFAC F-177", "MEGAFAC F-183", "MEGAFAC F-195", "MEGAFAC F-824", "MEGAFAC F-833", "MEGAFAC F-114", "MEGAFAC F-410", "MEGAFAC F-493", "MEGAFAC F-494", "MEGAFAC F-443", "MEGAFAC F-444", "MEGAFAC F-445", "MEGAFAC F-446", "MEGAFAC F-470", "MEGAFAC F-471", "MEGAFAC F-474", "MEGAFAC F-475", "MEGAFAC F-477", "MEGAFAC F-478", "MEGAFAC F-479", "MEGAFAC F-480SF", "MEGAFAC F-482", "MEGAFAC F-483", "MEGAFAC F-484", "MEGAFAC F-486", "MEGAFAC F-487", "MEGAFAC F-489", "MEGAFAC F-172D", "MEGAFAC F-178K", "MEGAFAC F-178RM", "MEGAFAC R-08", "MEGAFAC R-30", "MEGAFAC F-472SF", "MEGAFAC BL-20", "MEGAFAC R-61", "MEGAFAC R-90", "MEGAFAC ESM-1", and "MEGAFAC MCF-350SF" (manufactured by DIC Corporation);
"Ftergent 100", "Ftergent 100C", "Ftergent 110", "Ftergent 150", "Ftergent 150CH", "Ftergent A", "Ftergent 100A-K", "Ftergent 501", "Ftergent 300", "Ftergent 310", "Ftergent 320", "Ftergent 400SW", "FTX-400P", "Ftergent 251", "Ftergent 215M", "Ftergent 212MH", "Ftergent 250", "Ftergent 222F", "Ftergent 212D", "FTX-218", "FTX-209F", "FTX-213F", "FTX-233F", "Ftergent 245F", "FTX-208G", "FTX-240G", "FTX-206D", "FTX-220D", "FTX-230D", "FTX-240D", "FTX-207S", "FTX-211S", "FTX-220S", "FTX-230S", "FTX-750FM", "FTX-730FM", "FTX-730FL", "FTX-710FS", "FTX-710FM", "FTX-710FL", "FTX-750LL", "FTX-730LS", "FTX-730LM", "FTX-730LL", and "FTX-710LL" (manufactured by NEOS Company Limited);
"BYK-300", "BYK-302", "BYK-306", "BYK-307", "BYK-310", "BYK-315", "BYK-320", "BYK-322", "BYK-323", "BYK-325", "BYK-330", "BYK-331", "BYK-333", "BYK-337", "BYK-340", "BYK-344", "BYK-370", "BYK-375", "BYK-377", "BYK-350", "BYE-352", "BYK-354", "BYK-355", "BYK-356", "BYK-358N", "BYK-361N", "BYK-357", "BYK-390", "BYK-392", "BYK-UV3500", "BYK-UV3510", "BYK-UV3570", and "BYK-Silclean3700" (manufactured by BYK Japan KK); and
"TEGO Rad 2100", "TEGO Rad 2200N", "TEGO Rad 2250", "TEGO Rad 2300", "TEGO Rad 2500", "TEGO Rad 2600", and "TEGO Rad 2700" (manufactured by Tego).

The weight-average molecular weight of the compound represented by the general formula (VI) is preferably 200 to 100000, more preferably 300 to 10000, and further preferably 500 to 5000.

These surfactants and compounds represented by the general formula (VI) may each be used alone or in combination of two or more. The surfactant and the compound represented by the general formula (VI) may be combined with each other.

The total content of the surfactant and the compound represented by the general formula (VI) relative to the total weight of the solid content of the polymerizable liquid crystal composition according to this embodiment is preferably 0.01 to 1 wt % and more preferably 0.04 to 0.4 wt %.
<Other Components>

The composition according to this embodiment preferably contains a chain transfer agent as another component to further improve the adhesiveness to a substrate. The chain transfer agent is preferably a thiol compound, more preferably a monothiol compound, a dithiol compound, a trithiol compound, or a tetrathiol compound, and further preferably a trithiol compound. Specifically, compounds represented by general formulae (5-1) to (5-12) below are preferred.

The content of the thiol compound relative to the total weight of the solid content of the composition is preferably 0.5 to 7.0 wt % and more preferably 1.0 to 5.0 wt %.

[Chem. 16]

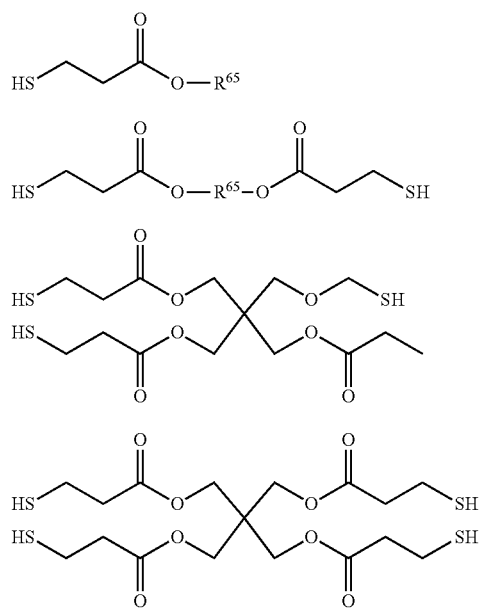
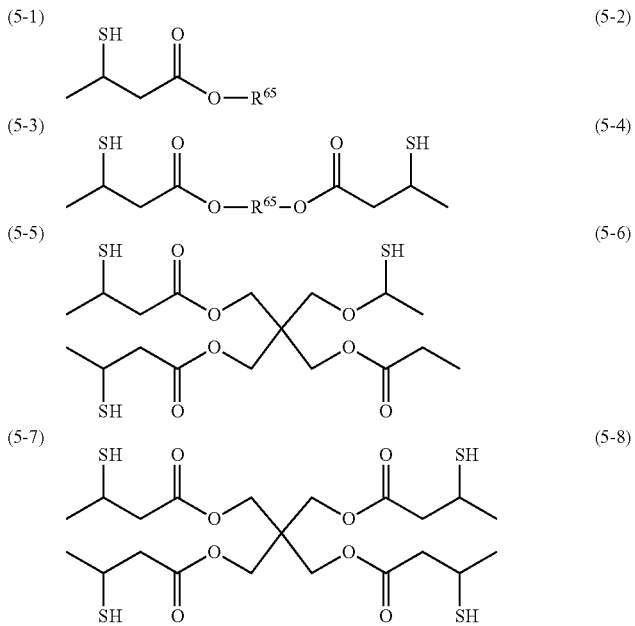

(5-9) 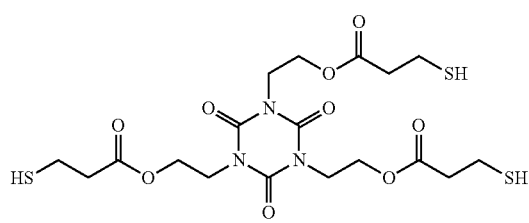

(5-10) 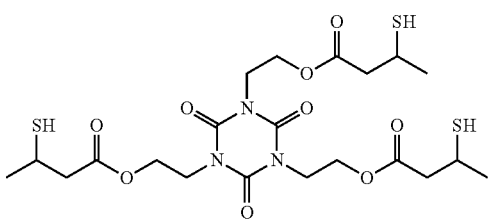

(5-11) 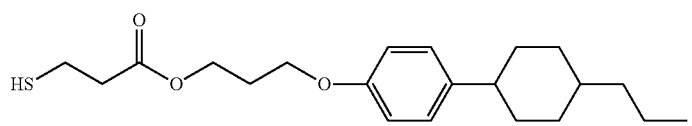

(5-12) 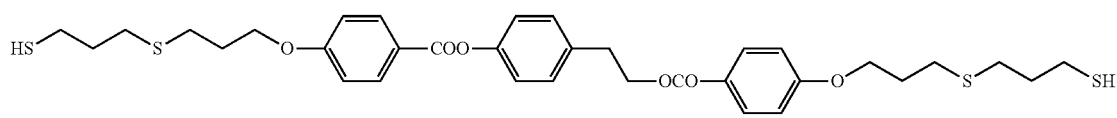

[in the formulae, $R^{65}$ represents an alkyl group having 2 to 18 carbon atoms. The alkyl group may have a linear chain or a branched chain. At least one methylene group in the alkyl group may be substituted with an oxygen atom, a sulfur atom, —CO—, —OCO—, —COO—, or —CH=CH— unless oxygen atoms and sulfur atoms directly bond to each other. $R^{66}$ represents an alkylene group having 2 to 18 carbon atoms. At least one methylene group in the alkylene group may be substituted with an oxygen atom, a sulfur atom, —CO—, —OCO—, —COO—, or —CH=CH— unless oxygen atoms and sulfur atoms directly bond to each other.]

The composition according to this embodiment preferably contains a polymerization inhibitor, an antioxidant, and the like to improve the storage stability. Examples of the compounds include hydroquinone derivatives and hindered phenol-based antioxidants. Specific examples of the compounds include p-methoxyphenol and IRGANOX 1010, IRGANOX 1035, IRGANOX 1076, IRGANOX 1098, IRGANOX 1135, IRGANOX 1330, IRGANOX 1425, IRGANOX 1520, IRGANOX 1726, IRGANOX 245, IRGANOX 259, IRGANOX 3114, IRGANOX 3790, IRGANOX 5057, and IRGANOX 565 manufactured by BASF.

The content of the polymerization inhibitor and the antioxidant relative to the total weight of the solid content of the composition is preferably 0.01 to 1.0 mass % and more preferably 0.02 to 0.2 mass %.

A liquid crystal compound having no polymerizability, a polymerizable compound having no liquid crystallinity, or the like may be optionally added to control the physical properties of the composition according to this embodiment.

The content of these compounds relative to the total weight of the solid content of the composition is preferably 20 wt % or less, more preferably 10 wt % or less, and further preferably 5 wt % or less.

<<Polymer, Optically Anisotropic Body, and Display>>

A polymer according to a third embodiment can be obtained by polymerizing the polymerizable compound according to the first embodiment contained in the composition according to the second embodiment by a publicly known method. The polymer is suitably used for production of optically anisotropic bodies such as retardation films, patterned retardation films, and homogeneously aligned liquid crystal films in the field of liquid crystal displays. The polymer is also suitably used as an antireflection film for organic EL displays.

Hereafter, a method for producing a retardation film will be described as an example. The polymerizable compound according to the first embodiment is used in the state of a solution prepared by dissolving the polymerizable compound in a solvent. The solution is applied onto the above-described substrate or the like, then dried, and polymerized by, for example, irradiation with ultraviolet rays or heat treatment to obtain a retardation film. An alignment treatment may be performed on the substrate in advance so that the polymerizable compound is easily aligned. In particular, the retardation film can be easily produced by using a photo-alignment film as an alignment treatment agent. The retardation pattern can also be changed by changing the temperature at which the solution applied to the substrate is heated.

A liquid crystal display device according to a fifth embodiment including the optically anisotropic body according to the fourth embodiment can be produced by incorporating the optically anisotropic body according to the fourth embodiment into a liquid crystal display device by a publicly known method.

Next, the present invention will be further described in detail based on Examples, but the present invention is not limited to these Examples. Note that "part" and "%" are on a mass basis unless otherwise specified.

EXAMPLES

Example 1

A polymerizable compound represented by formula (1-s-1) below was synthesized by the following method.

(1-s-1)

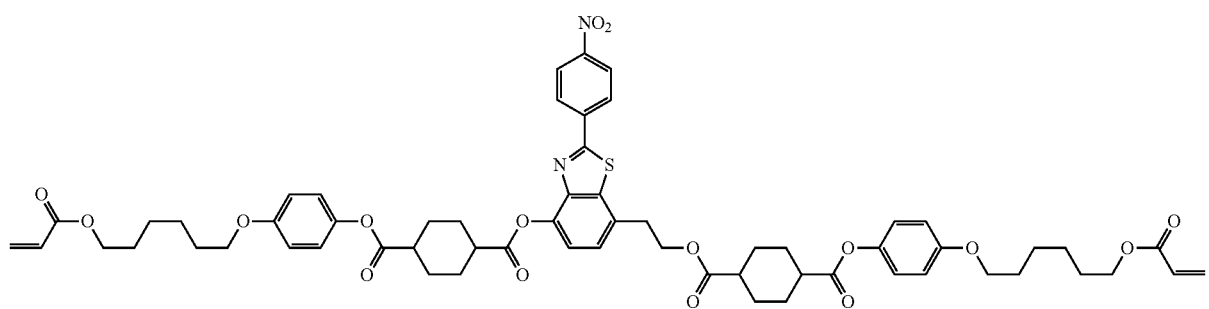

The upper-limit temperature of the phase sequence of the polymerizable compound (1-s-1) was determined by differential scanning calorimetry and by observing a liquid crystalline phase using a polarizing microscope equipped with a variable temperature controller. The upper-limit temperature was "C 89 S 110 N 179 Iso".

<Synthesis Method 1>

The polymerizable compound represented by the formula (1-s-1) below was synthesized by the following method.

[Chem. 18]

(1-s-1)

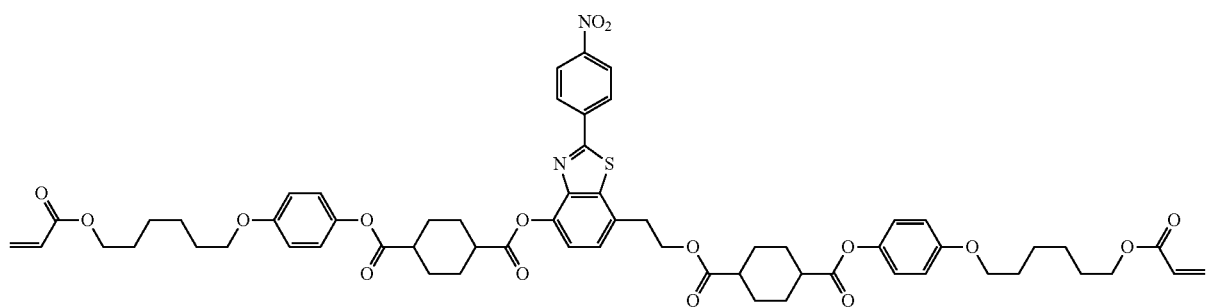

The synthesis scheme is shown below.

[Chem. 19]

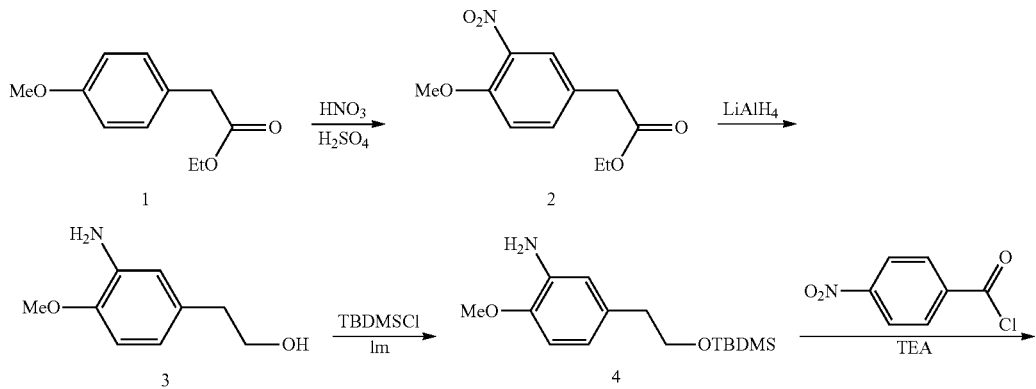

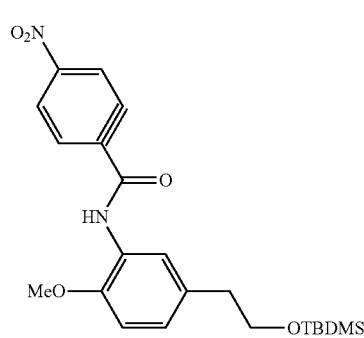
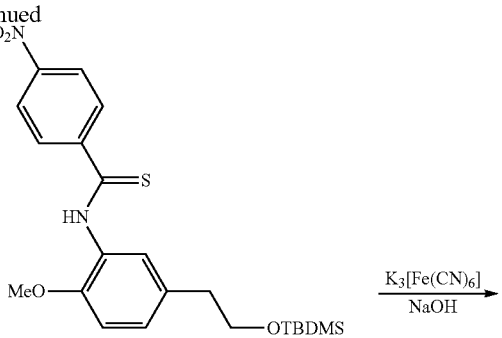
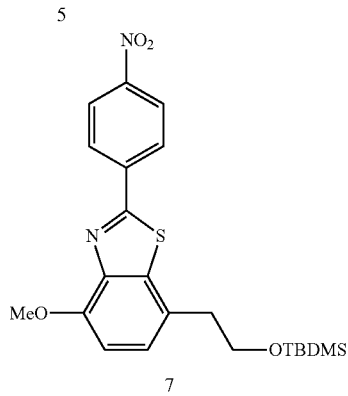
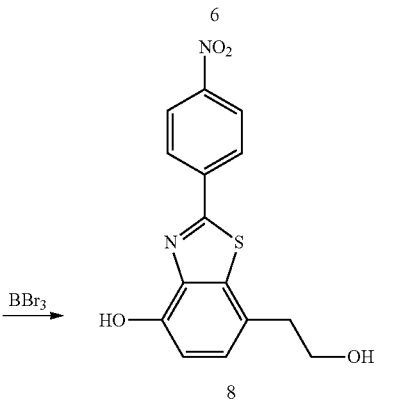
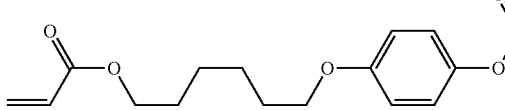

Synthesis Example of Compound (2)

Into a 300 ml four-neck flask, 19.4 g (100 mmol) of ethyl 4-methoxyphenylacetate (1) and 100 g of concentrated sulfuric acid were charged and dissolved under stirring. Under stirring, 6.7 g (110 mmol) of fuming nitric acid (specific gravity: 1.5) was added dropwise at −5° C. to 0° C. over 1 hour, and stirring was performed at the same temperature for 30 minutes. Subsequently, the resulting mixture was added to 300 g of ice water, and the precipitated crystal was filtered. The crystal was washed with 100 g of water, and 100 g of water was further added thereto. The crystal was washed by performing dispersion. The resulting crystal was filtered, washed with water, and dried to obtain 22.2 g of a compound (2) (yield: 93.0%).

Synthesis Example of Compound (3)

In a nitrogen atmosphere, 200 ml of dry tetrahydrofuran (THF) and 12.1 g (320 mmol) of lithium aluminum hydride were charged into a 500 ml four-neck flask and stirred at room temperature. Then, 19.1 g (80 mmol) of the compound (2) was dissolved in 100 ml of THF, and added dropwise at 40° C. or lower. After the dropwise addition, a reaction was caused to proceed under THF reflux for 3 hours. The reaction solution was cooled with ice, and 100 ml of 10% aqueous THF was added dropwise. Stirring was performed at room temperature for 2 hours, and the produced insoluble matter was removed by celite filtration. The filtrate was concentrated under reduced pressure to obtain 11.6 g of a compound (3) (yield: 87.0%).

Synthesis Example of Compound (4)

In a nitrogen atmosphere, 11.0 g (65.8 mmol) of the compound (3) and 200 mL of dimethylformamide (DMF) were charged into a 500 ml four-neck flask and stirred. At an internal temperature of 0° C., 9.0 g (131.6 mmol) of imidazole (Im) and 10.9 g (72.4 mmol) of chloro-t-butyldimethylsilane (TBDMSCl) were added thereto. The temperature was increased to room temperature, and stirring was performed for 16 hours. The reaction was stopped by adding 200 ml of water, and extraction was performed using ethyl acetate. The organic layer was dried with sodium sulfate. After the sodium sulfate was filtered off, the concentration was performed under reduced pressure. The resulting residue was purified by silica gel column chromatography (hexane/ethyl acetate=3/1) to obtain 18.1 g of a compound (4) (yield: 98.0%).

Synthesis Example of Compound (5)

In a nitrogen atmosphere, 17.5 g (62.2 mmol) of the compound (4), 6.9 g (68.4 mmol) of triethylamine (TEA), and 300 ml of dichloromethane were charged into a 500 ml four-neck flask and stirred. Under cooling with ice, a solution prepared by dissolving 12.1 g (65.3 mmol) of 4-nitrobenzoyl chloride in 50 ml of dichloromethane was added at 10° C. or lower. After the dropwise addition, the temperature was increased to room temperature, and a reaction was caused to proceed for 6 hours. The reaction solution was sequentially washed with water, 10% hydrochloric acid, and a saturated saline solution. After the concentration under reduced pressure, the resulting residue was purified by silica gel column chromatography (hexane/ethyl acetate=2/1) to obtain 25.8 g of a compound (5) (yield: 96.4%).

Synthesis Example of Compound (6)

In a nitrogen atmosphere, 24.0 g (55.7 mmol) of the compound (5), 13.3 g (32.8 mmol) of 2,4-bis(4-methoxyphenyl)-1,3-dithia-2,4-diphosphetane-2,4-disulfide (Lawesson's reagent), and 500 ml of toluene were charged into a 500 ml four-neck flask. The internal temperature was increased to 90° C. and stirring was performed for 5 hours. After cooling, the insoluble matter was filtered off. The filtrate was sequentially washed with a saturated sodium hydrogen carbonate solution and a saturated saline solution. The toluene was distilled off under reduced pressure. Then, the resulting residue was purified by silica gel column chromatography (hexane/ethyl acetate=3/1) to obtain 16.7 g of a compound (6) (yield: 67.2%).

Synthesis Example of Compound (7)

Into a four-neck flask (2 L), 16.0 g (35.8 mmol) of the compound (6), 43.0 g (1074 mmol) of sodium hydroxide, and 700 ml of water were charged and stirred. Under cooling with ice, 100 ml of an aqueous solution containing 23.6 g (71.6 mmol) of potassium ferricyanide was added to the resulting mixed solution. The precipitated solid was filtered and washed with cold water and hexane. The resulting solid was dried under reduced pressure to obtain 11.8 g of a compound (7) (yield: 74.1%).

Synthesis Example of Compound (8)

In a nitrogen atmosphere, 11.0 g (24.7 mmol) of the compound (7) and 150 ml of toluene were charged into a 300 ml four-neck flask and stirred. The mixed solution was cooled with ice, and 37.5 g (149 mmol) of boron tribromide ($BBr_3$) was added to the mixed solution at 5° C. or lower. After the dropwise addition, stirring was performed at room temperature for 3 hours. The reaction solution was added to 500 ml of ice water. The resulting precipitate was filtered and washed with water and toluene to obtain 6.1 g of a compound (8) (yield: 78.1%).

A compound (9) was synthesized by the following method.

[Chem. 20]

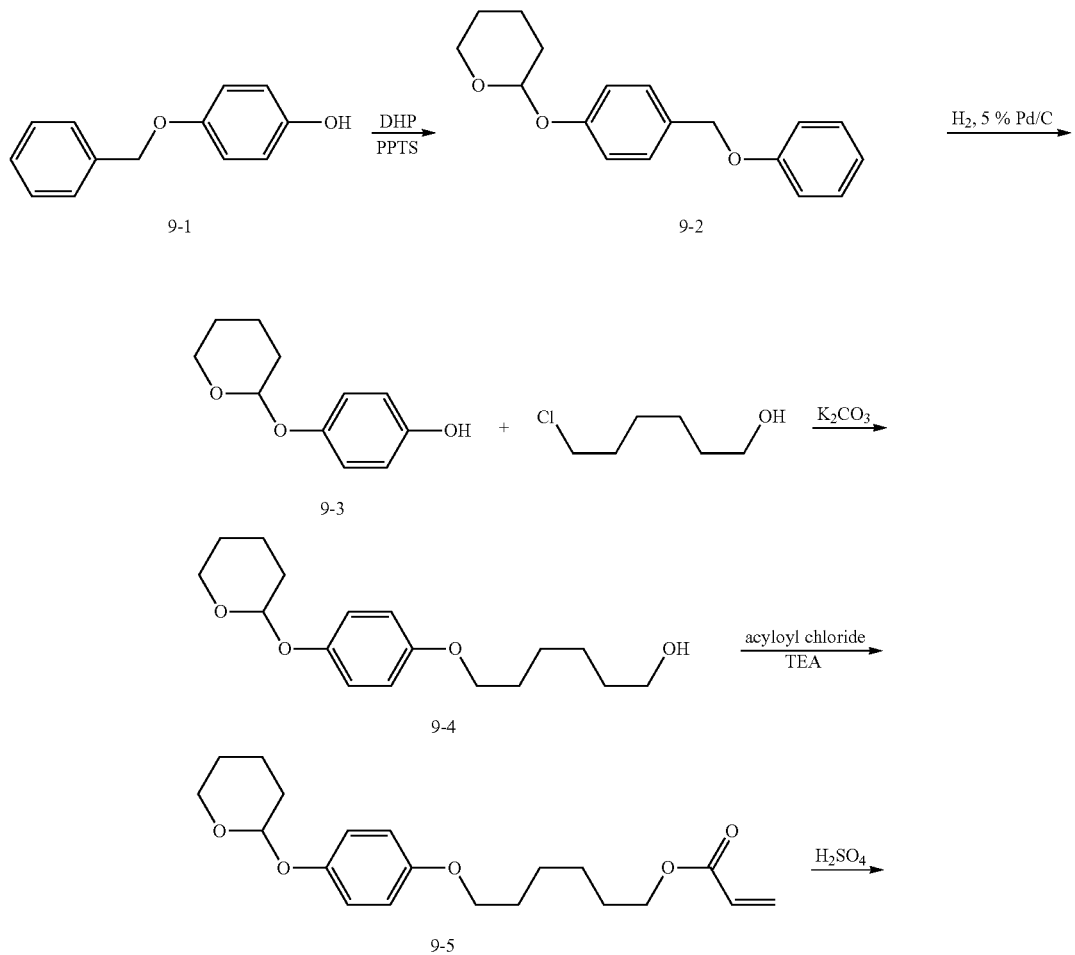

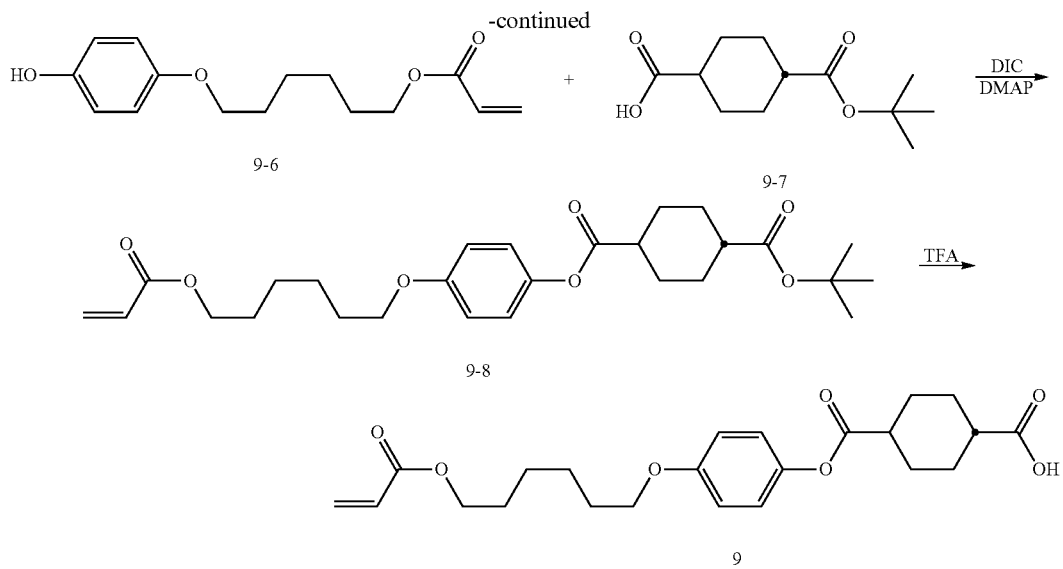

Synthesis of Compound (9-2)

In a nitrogen atmosphere, 40.0 g (200 mmol) of a compound (9-1), 1.0 g (4 mmol) of pyridinium p-toluenesulfonate (PPTS), and 200 ml of dichloromethane were charged into a 500 ml four-neck flask and stirred. Under cooling with ice, 25.2 g (300 mmol) of 3,4-dihydro-2H-pyran (DHP) was added dropwise. After the reaction was caused to proceed at room temperature for 8 hours, the reaction solution was sequentially washed with a saturated aqueous sodium hydrogen carbonate solution and a saturated saline solution. The organic layer was dried with sodium sulfate. The sodium sulfate was filtered off, and the concentration was performed under reduced pressure. Thus, 56.3 g of a compound (9-2) was obtained (yield: 99.0%).

Synthesis of Compound (9-3)

Into a 1 L autoclave, 56.3 g (198 mmol) of the compound (9-2), 2.8 g of a catalyst (5% Pd/C), and 250 ml of ethanol were charged. A reaction was caused to proceed at room temperature for 3 hours while a hydrogen pressure of 0.4 MPa was maintained. The catalyst was filtered off, and the concentration was performed under reduced pressure. Thus, 38.5 g of a compound (9-3) was obtained (quantitative).

Synthesis of Compound (9-4)

In a nitrogen atmosphere, 38.5 g of the compound (9-3), 41.0 g (297 mmol) of potassium carbonate, 27.0 g (198 mmol) of 6-chloro-1-hexanol, and 300 ml of dimethylformamide were charged into a 500 ml four-neck flask. The resulting mixed solution was heated to 100° C., and a reaction was caused to proceed for 24 hours. After cooling, extraction was performed by adding 600 ml of ethyl acetate and 600 ml of water. The organic layer was sequentially washed with water and a saturated saline solution, and dried with sodium sulfate. The sodium sulfate was filtered off and the concentration was performed under reduced pressure. Under cooling with ice, hexane was added to the concentrated residue to perform crystallization. The crystal was filtered and then dried under reduced pressure. Thus, 49.5 g of a compound (9-4) was obtained (yield: 84.9%).

Synthesis of Compound (9-5)

In a dry-air atmosphere, 44.2 g (150 mmol) of the compound (9-4), 16.7 g (165 mmol) of triethylamine (TEA), and 300 ml of dichloromethane were charged into a 500 ml four-neck flask and stirred. Then, 14.3 g (158 mmol) of acryloyl chloride was added dropwise at 5° C. or lower, and a reaction was caused to proceed at room temperature for 3 hours. The reaction solution was sequentially washed with water, dilute hydrochloric acid, saturated sodium hydrogen carbonate, and a saturated saline solution. The organic layer was dried with sodium sulfate. The sodium sulfate was filtered off and the concentration was performed under reduced pressure. Thus, 52.3 g of a compound (9-5) was obtained (quantitative).

Synthesis of Compound (9-6)

Into a 500 ml four-neck flask, 52.3 g (150 mmol) of the compound (9-5), 250 ml of tetrahydrofuran (THF), and 50 ml of methanol were charged and stirred. Then, 1.0 g of concentrated sulfuric acid was added to the resulting mixed solution, and a reaction was caused to proceed at room temperature for 3 hours. The reaction solution was added to 500 ml of ethyl acetate, and sequentially washed with a saturated aqueous sodium hydrogen carbonate solution and a saturated saline solution. The organic layer was concentrated, and the resulting residue was purified by silica gel column chromatography (dichloromethane). Thus, 32.4 g of a compound (9-6) was obtained (yield: 81.7%).

A compound (9-7) was synthesized by the following method.

[Chem. 21]

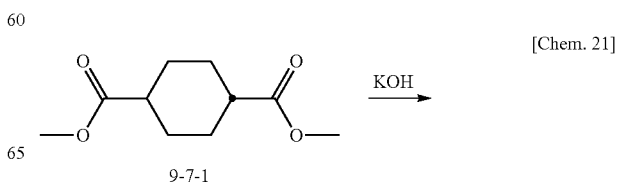

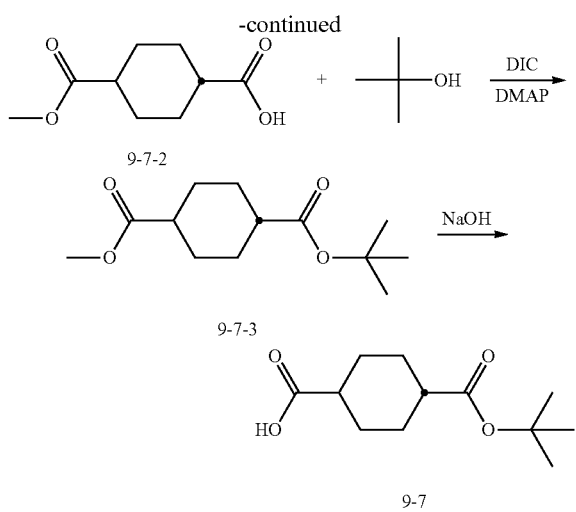

Synthesis of Compound (9-7-2)

Into a four-neck flask (1 L), 100.0 g (500 mmol) of dimethyl trans-1,4-cyclohexanedicarboxylate (9-7-1) and 1000 ml of methanol were charged and stirred. After 16.8 g (300 mmol) of potassium hydroxide was added, a reaction was caused to proceed under reflux for 6 hours. After cooling, the reaction solution was concentrated, and 500 ml of water was added to the residue. Dilute hydrochloric acid was added thereto until the pH reached 2, and the precipitated crystal was filtered. The crystal was washed with water and then dried under reduced pressure. Thus, 54.0 g of a compound (9-7-2) was obtained (yield: 58.0%).

Synthesis of Compound (9-7-3)

In a nitrogen atmosphere, 49.5 g (266 mmol) of the compound (9-7-2), 3.3 g (26.7 mmol) of N,N-dimethyl-4-aminopyridine (DMAP), 150 ml of tert-butyl alcohol, and 150 ml of tetrahydrofuran were charged into a 300 ml four-neck flask and uniformly stirred. Under cooling with ice, 50.4 g (399 mmol) of N,N'-diisopropylcarbodiimide (DIC) was added dropwise. A reaction was caused to proceed at room temperature for 6 hours, and 15 ml of water was added thereto. Stirring was further performed for 1 hour. The insoluble matter was filtered off, and the reaction solution was concentrated under reduced pressure. The resulting residue was purified by silica gel column chromatography (dichloromethane). Thus, 51.9 g of a compound (9-7-3) was obtained (yield: 80.6%).

Synthesis of Compound (9-7)

Into a four-neck flask (300 ml), 48.0 g (198 mmol) of the compound (9-7-3), 150 ml of methanol, and 150 ml of tetrahydrofuran were charged and stirred. Under cooling with ice, 24.0 g (600 mmol) of sodium hydroxide was added and stirring was performed at 5° C. or lower for 3 hours. The resulting mixture was added to 1000 ml of water and washed with dichloromethane. Dilute hydrochloric acid was added to the aqueous layer until the pH reached 2. The precipitated crystal was filtered, washed with water, and then dried under reduced pressure. Thus, 41.4 g of a compound (9-7) was obtained (yield: 91.6%).

Synthesis of Compound (9-8)

In a dry-air atmosphere, 29.0 g (128 mmol) of the compound (9-6), 34.4 g (130 mmol) of the compound (9-7), 0.6 g (15 mmol) of N,N-dimethyl-4-aminopyridine (DMAP), and 300 ml of dichloromethane were charged into a 500 ml four-neck flask and stirred. Under cooling with ice, 19.3 g (150 mmol) of N,N'-diisopropylcarbodiimide (DIC) was added dropwise. A reaction was caused to proceed at room temperature for 6 hours. Five milliliters of water was added thereto and stirring was further performed for 1 hour. After the insoluble matter was filtered off, the reaction solution was concentrated under reduced pressure. The resulting residue was purified by silica gel column chromatography (dichloromethane). Thus, 43.1 g of a compound (9-8) was obtained (yield: 71.1%).

Synthesis of Compound (9)

In a dry-air atmosphere, 42.0 g (88.5 mmol) of the compound (9-8) and 700 ml of dichloromethane were charged into a 2000 ml four-neck flask and stirred. Under cooling with ice, 100.8 g (885 mmol) of trifluoroacetic acid (TFA) was added dropwise, and a reaction was caused to proceed at room temperature for 8 hours. Then, 1000 ml of hexane was added thereto and the dichloromethane was distilled off under reduced pressure. The precipitated crystal was filtered and sequentially washed with water and hexane. The crystal was dried under reduced pressure to obtain 36.2 g of a compound (9) (yield: 97.8%).

Synthesis of Compound (1-s-1)

In a nitrogen atmosphere, 2.6 g (11 mmol) of the compound (8), 10.1 g (24 mmol) of the compound (9), 0.28 g (2 mmol) of N,N-dimethyl-4-aminopyridine (DMAP), and 80 ml of dichloromethane were charged into a 300 ml four-neck flask and stirred. Twenty milliliters of a dichloromethane solution containing 3.2 g (25 mmol) of diisopropylcarbodiimide (DIC) dissolved therein was added dropwise to the resulting mixed solution at 5° C. or lower. After the dropwise addition, a reaction was caused to proceed at room temperature for 4 hours. Then, 1 ml of water was added and stirring was further performed for 1 hour. After the insoluble matter was filtered off, the filtrate was washed with water and dried with sodium sulfate. The sodium sulfate was filtered off, and then the concentration was performed under reduced pressure. Two hundred milliliters of methanol was added to the residue and precipitation was caused under cooling with ice. The precipitate was filtered and sequentially washed with methanol and n-hexane. The resulting product was dried under reduced pressure to obtain 9.4 g of a compound (1-s-1) (yield: 77.3%).

<Production of Optical Film>

There was prepared a coating solution containing 19.32 wt % of the polymerizable compound (1-s-1) synthesized as described above, 0.60 wt % of Irgacure 907 (manufactured by Ciba Specialty Chemicals) serving as a polymerization initiator, 0.04 wt % of p-methoxyphenol (MEHQ) serving as a polymerization inhibitor, 0.04 wt % of BYK-361N (manufactured by BYK Japan KK) serving as a surfactant, and 80.00 wt % of chloroform serving as a solvent.

Subsequently, the coating solution was applied onto a glass substrate with polyimide subjected to a rubbing treatment by a spin coating method. The coating solution was dried on a hot plate at 80° C. for 1 minute, then further dried at 140° C. for 1 minute, and irradiated at 140° C. with ultraviolet rays having 1000 mJ/cm$^2$ to produce an optical film (optically anisotropic body) having a thickness of 1.02 µm.

<Measurement of Optical Properties>

The retardation of the produced optical film was measured with a measurement device (RET-100 manufactured by Otsuka Electronics Co., Ltd.) in the wavelength range of 450 nm to 700 nm. The retardation Re(450) at a wavelength of 450 nm, the retardation Re(550) at a wavelength of 550 nm, and the retardation Re(650) at a wavelength of 650 nm were calculated using a program included with the device. Table 1 shows the results.

TABLE 1

|  | Re(550) (nm) | Re(450)/ Re(550) | Re(650)/ Re(550) | Thickness d (μm) | Δn |
|---|---|---|---|---|---|
| Example 1 | 71.2 | 0.870 | 1.050 | 1.02 | 0.070 |
| Example 2 | 71.2 | 0.861 | 1.051 | 0.99 | 0.072 |
| Example 3 | 63.2 | 0.921 | 1.038 | 1.02 | 0.062 |
| Comparative Example 1 | 56.5 | 0.848 | 1.033 | 1.01 | 0.056 |

Example 2

A polymerizable compound represented by formula (1-s-2) below was synthesized by the following method.

[Chem. 22]

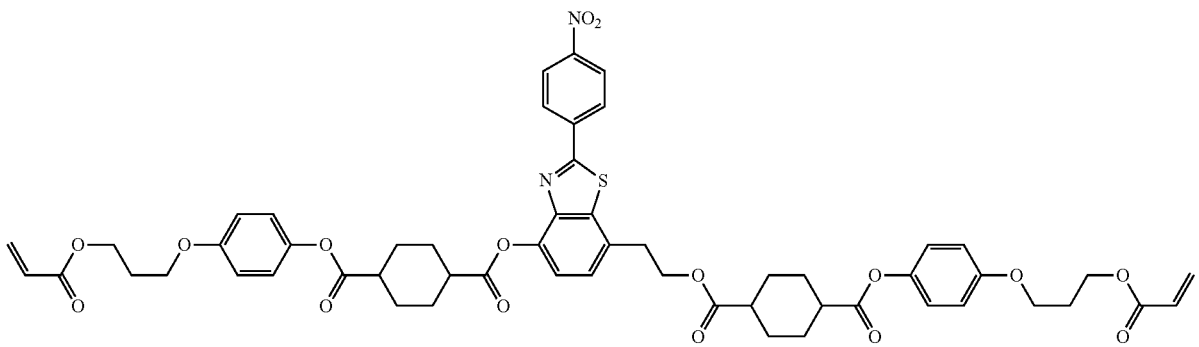

(1-s-2)

The upper-limit temperature of the phase sequence of the polymerizable compound (1-s-2) was determined by differential scanning calorimetry and by observing a liquid crystalline phase using a polarizing microscope equipped with a variable temperature controller. The upper-limit temperature was "C 80 S 102 N 165 Iso".

<Synthesis Method 2>

The compound (1-s-2) was synthesized by a method similar to that of Synthesis Example 1.

<Production of Optical Film>

A coating solution was prepared in the same manner as in Example 1, except that the polymerizable compound (1-s-2) was used in the same amount instead of the polymerizable compound (1-s-1) used in Example 1.

Subsequently, the coating solution was applied onto a glass substrate with polyimide subjected to a rubbing treatment by a spin coating method. The coating solution was dried on a hot plate at 80° C. for 1 minute, then further dried at 100° C. for 1 minute, and irradiated at 90° C. with ultraviolet rays having 1000 mJ/cm$^2$ to produce an optical film (optically anisotropic body) having a thickness of 0.99 μm.

<Measurement of Optical Properties>

The optical properties of the produced optical film were measured in the same manner as in Example 1. Table 1 also shows the results.

Example 3

A polymerizable compound represented by formula (1-t-1) below was synthesized by the following method.

[Chem. 23]

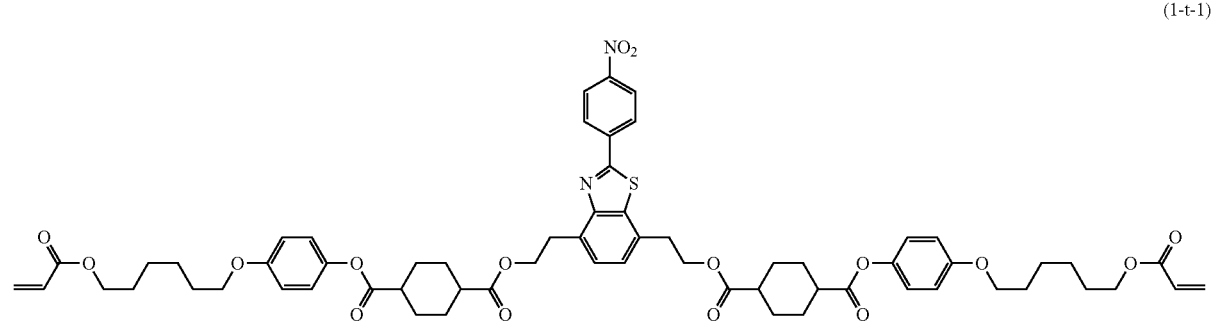

(1-t-1)

The upper-limit temperature of the phase sequence of the polymerizable compound (1-t-1) was determined by differential scanning calorimetry and by observing a liquid crystalline phase using a polarizing microscope equipped with a variable temperature controller. The upper-limit temperature was "C 85 S 99 N 135 Iso".

<Synthesis Method 3>

The compound (1-t-1) was synthesized by a method similar to that of Synthesis Example 1.

<Production of Optical Film>

A coating solution was prepared in the same manner as in Example 1, except that the polymerizable compound (1-t-1) was used in the same amount instead of the polymerizable compound (1-s-1) used in Example 1.

Subsequently, the coating solution was applied onto a glass substrate with polyimide subjected to a rubbing treatment by a spin coating method. The coating solution was dried on a hot plate at 80° C. for 1 minute, then further dried at 100° C. for 1 minute, and irradiated at 90° C. with ultraviolet rays having 1000 mJ/cm² to produce an optical film (optically anisotropic body) having a thickness of 1.02 µm.

<Measurement of Optical Properties>

The optical properties of the produced optical film were measured in the same manner as in Example 1. Table 1 also shows the results.

Comparative Example 1

A polymerizable compound represented by formula (Ref1) below was synthesized by the following method.

[Chem. 24]

(Ref1)

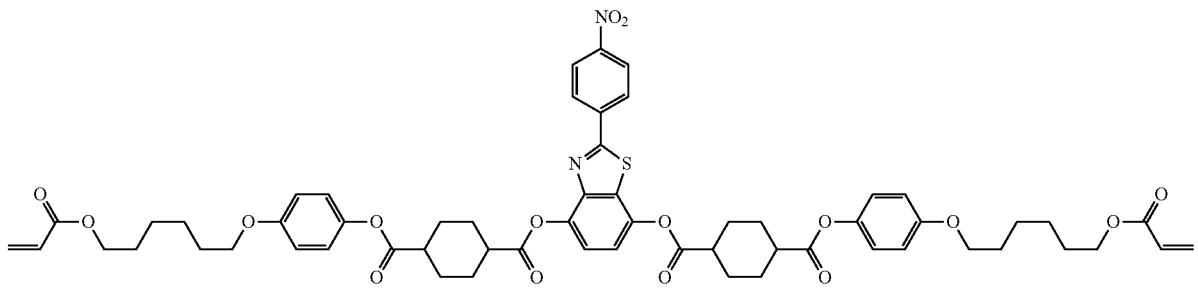

The upper-limit temperature of the phase sequence of the polymerizable compound (Ref1) was determined by differential scanning calorimetry and by observing a liquid crystalline phase using a polarizing microscope equipped with a variable temperature controller. The upper-limit temperature was "C 160 S 169 N 224 Iso".

<Synthesis Method 4>

The compound (Ref1) was obtained by a method described in Japanese Unexamined Patent Application Publication No. 2010-31223.

<Production of Optical Film>

A coating solution was prepared in the same manner as in Example 1, except that the polymerizable compound (Ref1) was used in the same amount instead of the polymerizable compound (1-s-1) used in Example 1.

Subsequently, the coating solution was applied onto a glass substrate with polyimide subjected to a rubbing treatment by a spin coating method. The coating solution was dried on a hot plate at 80° C. for 1 minute, then further dried at 210° C. for 1 minute, and irradiated at 190° C. with ultraviolet rays having 1000 mJ/cm² to produce an optical film (optically anisotropic body) having a thickness of 1.01 µm.

<Measurement of Optical Properties>

The optical properties of the produced optical film were measured in the same manner as in Example 1. Table 1 also shows the results.

As described above, the polymerizable compounds in Examples 1 to 3 have better reverse wavelength dispersibility than the polymerizable compound in Comparative Example. Therefore, it is obvious that optically anisotropic bodies having excellent optical properties can be produced by using the polymerizable compounds in Examples 1 to 3.

Furthermore, by using the polymerizable compounds in Examples 1 to 3, optical films can be produced at a low temperature compared with Comparative Example 1. Since degradation at a high temperature does not occur, the uniformity of the alignment of the optical films in Examples 1 to 3 is better than that in Comparative Example 1, and thus Δn (refractive index anisotropy) is improved.

One of the reasons for which the optical films in Examples 1 to 3 have excellent properties may be as follows: the polymerizable compound includes, as the divalent linking groups represented by $X^1$, $X^2$, $X^3$, and $X^4$ in the general formula (1), at least one linking group selected from the group consisting of —$CH_2CH_2COO$—, —$CH_2CH_2OOC$—, —$COOCH_2CH$—, and —$OOCCH_2CH_2$—, each of which has an ethylene group. Such a linking group is believed to contribute to the above-described improvement in optical properties by imparting structural flexibility without degrading the alignment of the polymerizable compound. Furthermore, in the major-axis direction of the molecule represented by the general formula (1), the divalent linking groups represented by $X^2$ (left) and $X^3$ (right) constitute an asymmetrical chemical structure, which is believed to contribute to the above-described improvement in optical properties.

The structures and the combinations thereof in the above-described embodiments are merely examples. The additions, omissions, substitutions, and other modifications of the structures can be made without departing from the spirit of the present invention. Furthermore, the present invention is not limited by the embodiments, but is limited by only the scope of the claims.

INDUSTRIAL APPLICABILITY

The polymerizable compound according to the present invention can be widely applied to the field of liquid crystal displays.

The invention claimed is:

1. A polymerizable compound represented by general formula (1):

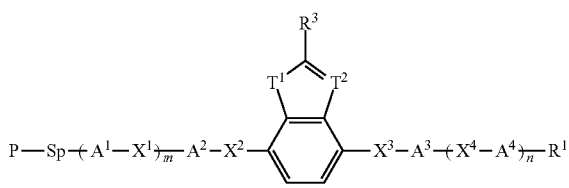

(1)

[in the formula, P represents a polymerizable functional group and Sp represents a spacer group or a single bond, $A^1$, $A^2$, $A^3$, and $A^4$ each independently represent a divalent alicyclic hydrocarbon group or aromatic hydrocarbon group, $X^1$, $X^2$, $X^3$, and $X^4$ each independently represent a divalent linking group or a single bond (at least one of $X^1$, $X^2$, $X^3$, and $X^4$ represents one of linking groups selected from —CH$_2$CH$_2$COO—, —CH$_2$CH$_2$OCO—, —COOCH$_2$CH$_2$—, —OCOCH$_2$CH$_2$—, —CH=CH—, —CH=CHCOO—, —OCOCH=CH—, —N=N—, —N=C—, and —C=N—N=C—), wherein a combination of $X^2$ and $X^3$ (hereafter expressed as "$X^2/X^3$") in the general formula (1) is as follows:

"—COO—(CH$_2$)$_u$—/—CH$_2$CH$_2$—COO—", "—COO—(CH$_2$)$_u$—/—COO—CH$_2$CH$_2$—",
"—COO—(CH$_2$)$_u$—/—OCO—CH$_2$CH$_2$—", "—COO—(CH$_2$)$_u$—/—CH$_2$CH$_2$—OCO—",
"—OCO—(CH$_2$)$_u$—/—CH$_2$CH$_2$—COO—", "—OCO—(CH$_2$)$_u$—/—COO—CH$_2$CH$_2$—",
"—OCO—(CH$_2$)$_u$—/—OCO—CH$_2$CH$_2$—", "—OCO—(CH$_2$)$_u$—/—CH$_2$CH$_2$—OCO—",
"—OCO—CH$_2$CH$_2$—/—COO—(CH$_2$)$_u$—", "—CH$_2$CH$_2$—OCO—/—COO—(CH$_2$)$_u$—",
"—CH$_2$CH$_2$—COO—/—(CH$_2$)$_u$—", "—COO—CH$_2$CH$_2$—/—COO—(CH$_2$)$_u$—",
"—OCO—CH$_2$CH$_2$—/—OCO—(CH$_2$)$_u$—", "—CH$_2$CH$_2$—OCO—/—OCO—(CH$_2$)$_u$—",
"—CH$_2$CH$_2$—COO—/—OCO(CH$_2$)$_u$—", "—COO—CH$_2$CH$_2$—/—OCO—(CH$_2$)$_u$—",
(u represents an integer of 0 to 2)
"single bond/—CH$_2$CH$_2$—COO—", "single bond/—COO—CH$_2$CH$_2$—",
"single bond/—OCO—CH$_2$CH$_2$—", "single bond/—CH$_2$CH$_2$—OCO—",
"—OCO—CH$_2$CH$_2$—/single bond", "—CH$_2$CH$_2$—OCO—/single bond",
"—CH$_2$CH$_2$—COO—/single bond", or "—COO—CH$_2$CH$_2$—/single bond,"

$R^1$ represents an alkyl group having 1 to 12 carbon atoms, an alkoxy group having 1 to 12 carbon atoms, or "*-Sp-P" (* represents a bond with $A^4$ or $A^3$), $R^3$ represents an alkyl group having 1 to 6 carbon atoms, an alicyclic hydrocarbon group, or an aromatic hydrocarbon group, wherein a hydrogen atom in the alicyclic hydrocarbon group or the aromatic hydrocarbon group may be substituted with an alkyl group having 1 to 6 carbon atoms, an alkoxy group having 1 to 6 carbon atoms, a halogen atom, a cyano group, a nitro group, a —C≡C—CH$_3$ group, or a hydroxy group, m and n each independently represent an integer of 0 to 4 (m+n is an integer of 2 or more), $T^1$ represents —S—, —O—, —CH$_2$—, —NH—, —C(=O)—, —S(=O)—, or —C(=S)—, $T^2$ represents =CR$^2$— or =N—, and $R^2$ represents a hydrogen atom, a halogen atom, an alkyl group having 1 to 6 carbon atoms, an alkoxy group having 1 to 6 carbon atoms, a cyano group, a nitro group, or a hydroxy group].

2. The polymerizable compound according to claim 1, wherein a group that links $X^2$ and $X^3$ in the general formula (1) is a group represented by one of general formulae (2-1) to (2-5) below:

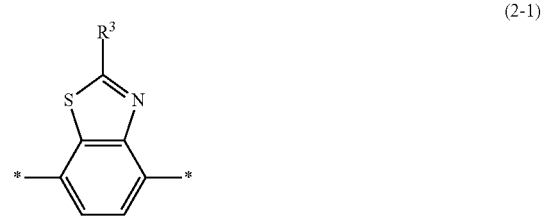

(2-1)

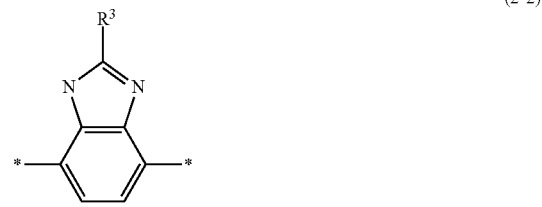

(2-2)

(2-3)

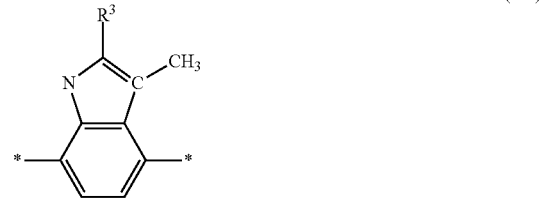

(2-4)

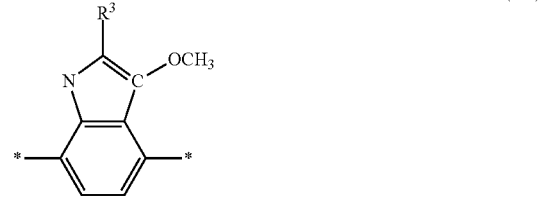

(2-5)

[in the formulae, "*" represent bonds with $X^2$ and $X^3$ in the general formula (1), and $R^3$ is the same as $R^3$ in the general formula (1)].

3. The polymerizable compound according to claim 1,
wherein $R^3$ in the general formula (1) represents a phenyl group or a cyclohexylene group, and a hydrogen atom that bonds to the phenyl group or the cyclohexylene group may be substituted with an alkyl group having 1 to 6 carbon atoms, an alkoxy group having 1 to 6 carbon atoms, a halogen atom, a cyano group, a nitro group, a —C≡C—CH$_3$ group, or a hydroxy group.

4. A composition comprising the polymerizable compound according to claim 1.

5. A polymer obtained by polymerizing the composition according to claim 4.

6. An optically anisotropic body using the polymer according to claim 5.

7. A liquid crystal display device using the optically anisotropic body according to claim 6.

8. An organic EL device using the optically anisotropic body according to claim 6.

9. The organic EL device according to claim 8, wherein the organic EL device means an organic electroluminescence device.

* * * * *